(12) United States Patent
Chida et al.

(10) Patent No.: US 11,065,020 B2
(45) Date of Patent: Jul. 20, 2021

(54) SUCTION CATHETER, SUCTION SYSTEM, AND TREATMENT METHOD

(71) Applicant: TERUMO KABUSHIKI KAISHA, Tokyo (JP)

(72) Inventors: Takahiro Chida, Kanagawa (JP); Masaomi Imai, Kofu (JP); Yuki Masubuchi, Hadano (JP); Takashi Kitaoka, Hadano (JP); Kazuaki Kanamoto, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 234 days.

(21) Appl. No.: 16/288,425

(22) Filed: Feb. 28, 2019

(65) Prior Publication Data
US 2019/0192175 A1   Jun. 27, 2019

Related U.S. Application Data

(63) Continuation of application No. PCT/JP2017/030306, filed on Aug. 24, 2017.

(30) Foreign Application Priority Data

Aug. 29, 2016 (JP) .............................. JP2016-166615

(51) Int. Cl.
*A61B 17/221* (2006.01)
*A61B 17/3207* (2006.01)
(Continued)

(52) U.S. Cl.
CPC ............ *A61B 17/221* (2013.01); *A61B 17/22* (2013.01); *A61B 17/3207* (2013.01);
(Continued)

(58) Field of Classification Search
CPC ... A61B 17/22; A61B 17/221; A61B 17/3207; A61B 17/32075; A61B 17/230758;
(Continued)

(56) References Cited

U.S. PATENT DOCUMENTS 5,827,229 A   10/1998   Auth et al.
5,938,645 A    8/1999   Gordon
(Continued)

FOREIGN PATENT DOCUMENTS

JP   S60113046 U   7/1985
JP   H11114069 A   4/1999
(Continued)

OTHER PUBLICATIONS

International Search Report (with English translation) and Written Opinion issued in corresponding International Patent Application No. PCT/JP2017/030306, 12 pages (dated Nov. 28, 2017).

*Primary Examiner* — Jocelin C Tanner
(74) *Attorney, Agent, or Firm* — Buchanan Ingersoll & Rooney PC

(57) ABSTRACT

A method for suctioning an object in a blood vessel, the method comprising: inserting an expansion portion connected to a shaft portion on a distal portion of the shaft portion into the blood vessel; expanding the expansion portion in the blood vessel; inserting a suction catheter along the shaft portion into the blood vessel; reciprocating at least the expansion portion or the suction catheter relative to each other along an axial axis of the shaft portion; and suctioning the object with the suction catheter.

19 Claims, 31 Drawing Sheets

(51) Int. Cl.
 *A61B 17/22* (2006.01)
 *A61M 25/00* (2006.01)
(52) U.S. Cl.
 CPC ....... *A61M 25/00* (2013.01); *A61B 17/32075* (2013.01); *A61B 17/320758* (2013.01); *A61B 2017/22039* (2013.01); *A61B 2017/22047* (2013.01); *A61B 2017/22079* (2013.01); *A61B 2017/320716* (2013.01); *A61B 2217/005* (2013.01); *A61M 25/0074* (2013.01); *A61M 25/0082* (2013.01)
(58) Field of Classification Search
 CPC .......... A61B 2017/22039; A61B 2017/22047; A61B 2017/22079; A61B 2017/320716; A61B 2217/005; A61M 25/00; A61M 25/007; A61M 25/0074; A61M 25/0082; A61M 29/02
 See application file for complete search history.

(56) References Cited

U.S. PATENT DOCUMENTS

| | | | |
|---|---|---|---|
| 6,039,723 A | 3/2000 | Tanaka et al. | |
| 2003/0023263 A1 | 1/2003 | Krolik et al. | |
| 2005/0004594 A1* | 1/2005 | Noo | 606/200 |
| 2006/0025806 A1 | 2/2006 | Krolik et al. | |
| 2007/0060908 A1 | 3/2007 | Webster et al. | |
| 2007/0060911 A1 | 3/2007 | Webster et al. | |
| 2007/0060944 A1 | 3/2007 | Boldenow et al. | |
| 2007/0208370 A1* | 9/2007 | Hauser | A61F 2/01 606/200 |
| 2008/0154186 A1 | 6/2008 | Appling et al. | |
| 2012/0116440 A1* | 5/2012 | Leynov | A61B 17/221 606/200 |
| 2014/0052103 A1* | 2/2014 | Cully | A61B 17/221 604/508 |
| 2016/0113662 A1* | 4/2016 | Kobayashi | A61F 2/013 606/127 |
| 2016/0331506 A1* | 11/2016 | Korkuch | A61F 2/013 |
| 2017/0224463 A1 | 8/2017 | Kobayashi et al. | |

FOREIGN PATENT DOCUMENTS

| | | |
|---|---|---|
| JP | 2004535885 A | 12/2004 |
| JP | 2007527264 A | 9/2007 |
| JP | 2009504343 A | 2/2009 |
| JP | 2010099215 A | 5/2010 |
| JP | 2013202115 A | 10/2013 |
| WO | 1998044982 A1 | 10/1998 |
| WO | 2016067646 A1 | 5/2016 |

\* cited by examiner

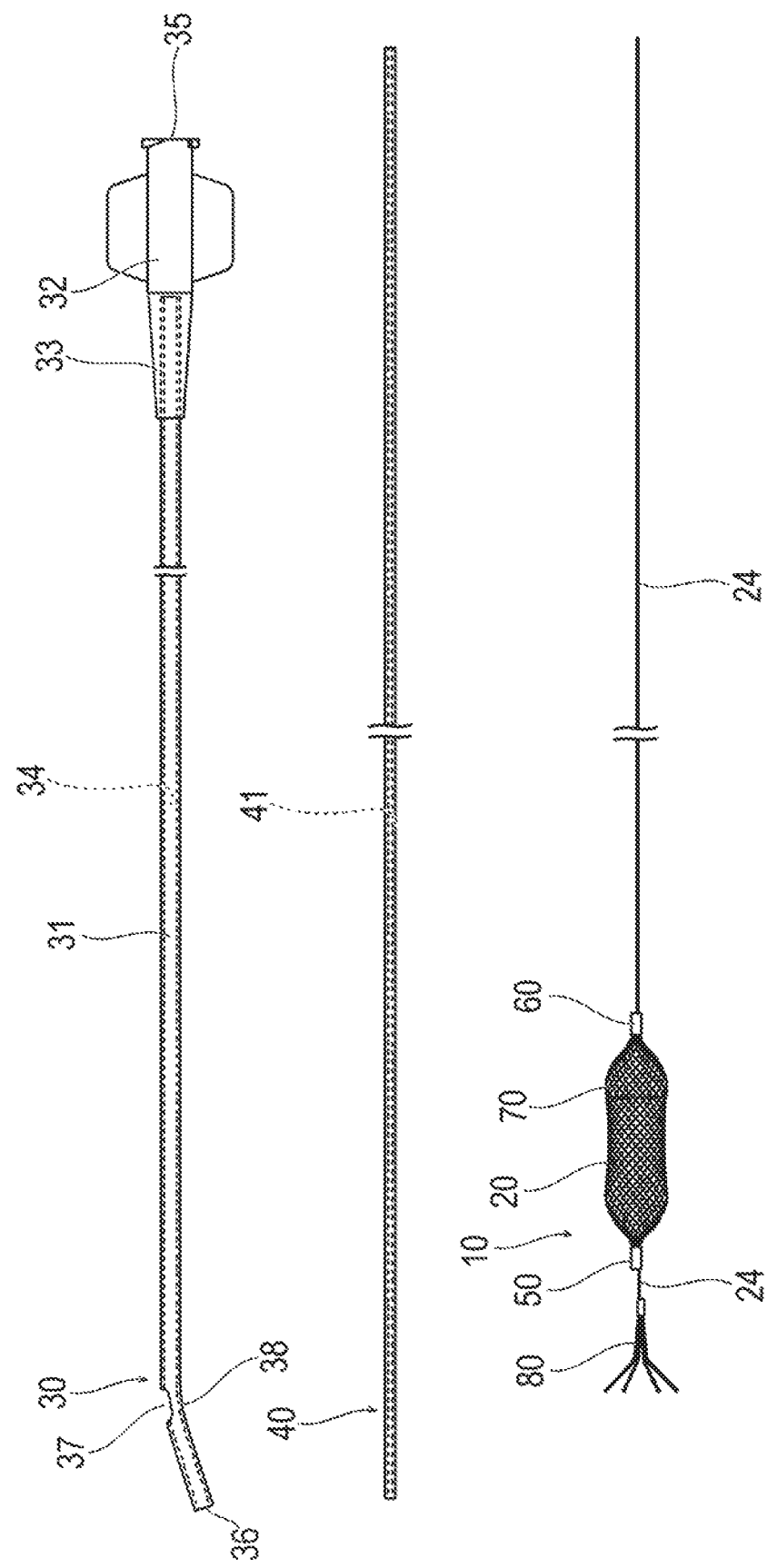

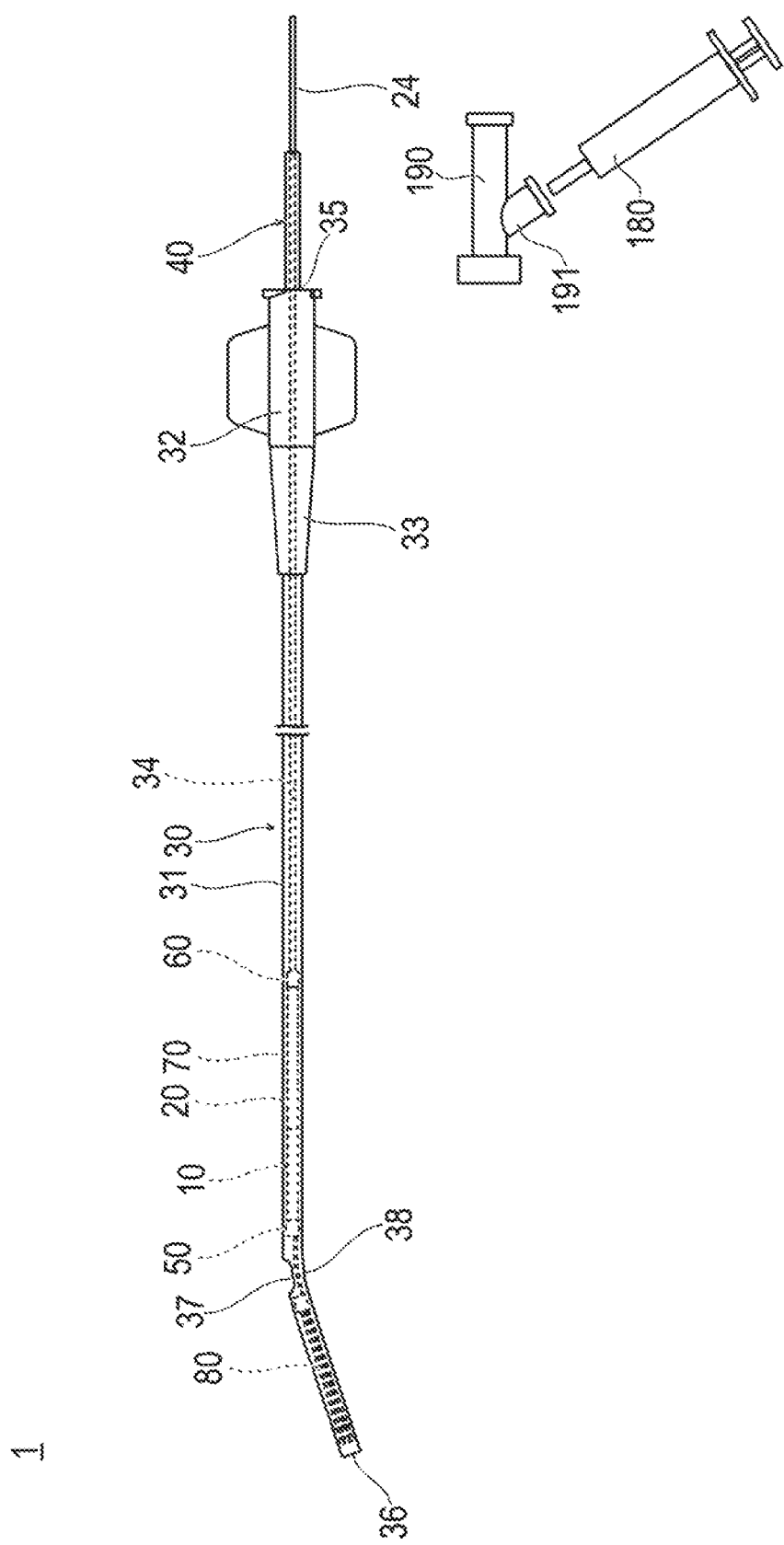

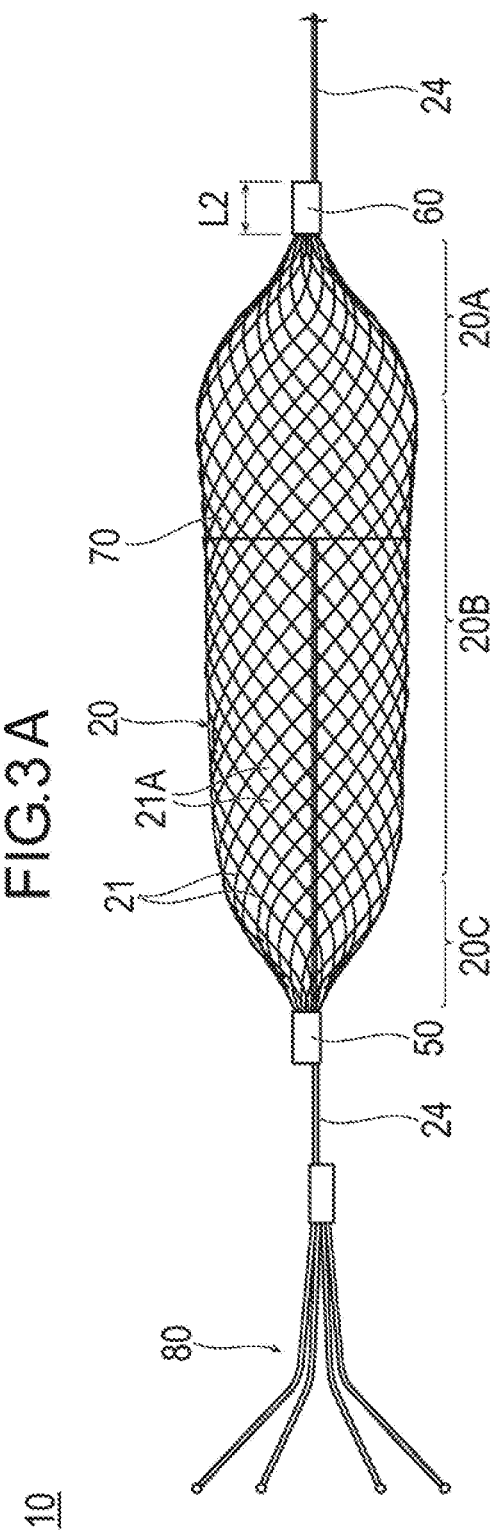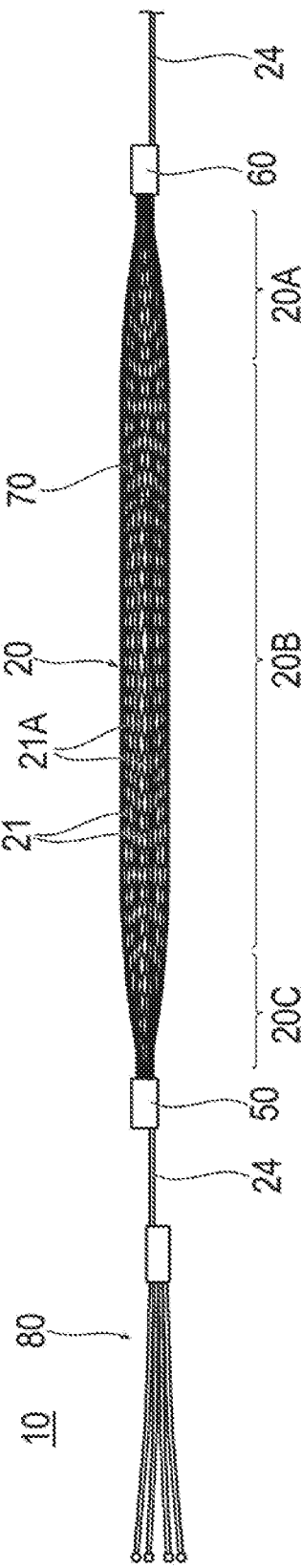

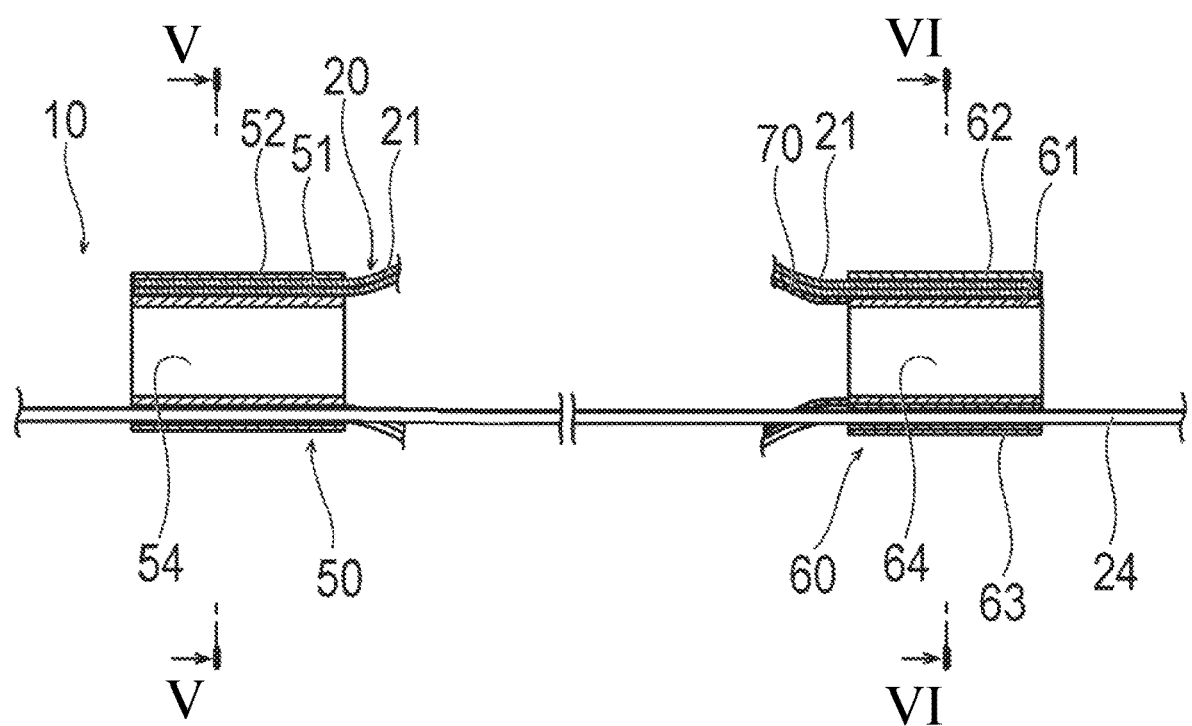

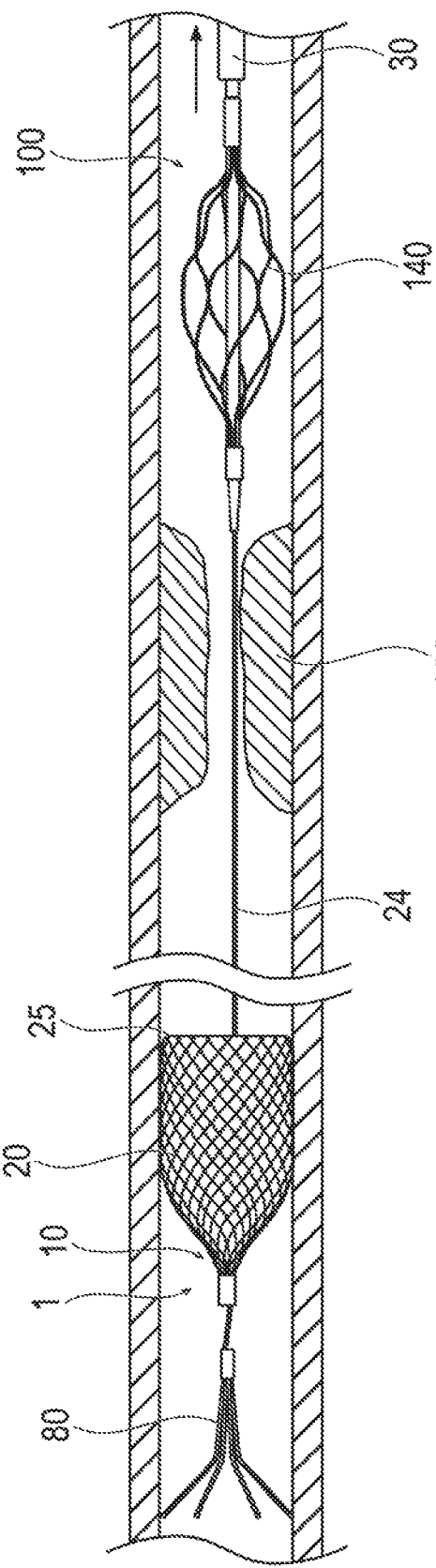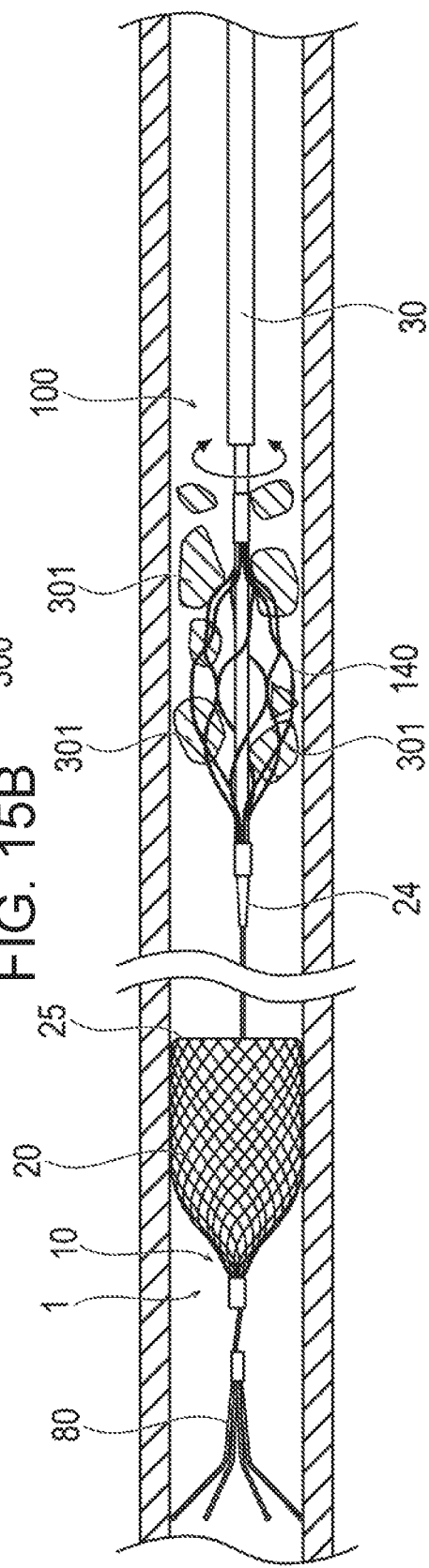

SUCTION CATHETER, SUCTION SYSTEM, AND TREATMENT METHOD

CROSS-REFERENCES TO RELATED APPLICATIONS

This application is a continuation of International Application No. PCT/JP2017/030306 filed on Aug. 24, 2017, which claims priority to Japanese Application No. 2016-166615 filed on Aug. 29, 2016, the entire content of both of which is incorporated herein by reference.

FIELD OF THE DISCLOSURE

The present disclosure relates to a suction catheter and a suction system configured to be inserted into a biological lumen, and a treatment method using the suction system.

BACKGROUND DISCUSSION

Blood clots in part of a vein may cause a pain or a swelling. Examples of a treatment of such clots include a method of physically breaking and removing the blood clots by percutaneously inserting a device. Such a treatment has a risk of pulmonary embolism when blood clots completely or partly separated from a vascular wall flow on a blood flow and reach the lungs. Therefore, when performing such a treatment, a thrombolytic agent is used before and/or after, or during the treatment, or separated blood clots are removed by suction as much as possible during the treatment. However, even when such a procedure is performed, separated blood clots having a clinically problematic size may reach the lungs or the like.

In order to avoid an occurrence of the pulmonary embolism, a method of indwelling a filter configured to trap blood clots flowing in the blood vessel is known. For example, U.S. Patent Application Publication No. 2005/0004594 discloses a method of placing a filter for trapping blood clots at a distal portion of a longitudinally extending wire and inserting a suction catheter for suctioning the blood clots on a proximal side. The suction catheter is introduced to an intended position along the wire fixed to the filter. The suction catheter then suctions (i.e., sucks) and removes the blood clots trapped by the filter to outside the body.

The suction catheter includes a main suction port in an end surface provided on a distal side and extending vertical to a central axis. Therefore, the suction catheter may be subjected to clogging of a suction port by blood clots having a diameter larger than a diameter of a suction lumen of the suction catheter and thus may fail to effectively remove the blood clots. In addition, the position of the suction catheter with respect to a filter differs depending on operators. Therefore, the procedure depends on the operator and thus is not stabilized.

SUMMARY

In accordance with an exemplary embodiment, a suction catheter and a suction system capable of effectively removing an object flowing in a biological lumen and providing a stable procedure, and a treatment method are disclosed.

In accordance with an exemplary embodiment, a suction catheter is disclosed, which is configured to be inserted into a biological lumen and capable of suctioning an object in the biological lumen, the suction catheter including: a base member having a tubular shape; and a distal side tubular portion having a tubular shape and located at a distal side of the base member, the distal side tubular portion inclining toward a predetermined direction with respect to a central axis of the base member, wherein the distal side tubular portion includes a distal side opening inclining with respect to a central axis of the distal side tubular portion and provided at a distal end, and the distal side opening opens toward a direction opposite from a direction of inclination of the distal side tubular portion with respect to the base member.

In accordance with an exemplary embodiment, a suction system is disclosed, which is configured to be inserted into a biological lumen and capable of trapping and suctioning an object in the biological lumen, the suction system including: a shaft portion having an elongated shape; an expansion portion being a cylindrical member, the cylindrical member including a plurality of gaps and being resiliently deformable; a proximal side coupling portion provided on a proximal side of the expansion portion and coupled fixedly or movably to the shaft portion; and a suction catheter movably accommodating the shaft portion and being provided with a suction lumen for making a suction force act, wherein the suction catheter includes a base member having a tubular shape, and a distal side tubular portion having a tubular shape and located at a distal side of the base member, the distal side tubular portion inclining toward a predetermined direction with respect to a central axis of the base member, the distal side tubular portion includes a distal side opening inclining with respect to a central axis of the distal side tubular portion and provided at a distal end, and the distal side opening opens toward a direction opposite from a direction of inclination of the distal side tubular portion with respect to the base member.

In accordance with an exemplary embodiment, a suction system is disclosed, which is configured to be inserted into a biological lumen and capable of trapping and suctioning an object in the biological lumen, the suction system including: a shaft portion having an elongated shape; an expansion portion being a cylindrical member, the cylindrical member including a plurality of gaps and being resiliently deformable; a proximal side coupling portion provided on a proximal side of the expansion portion and coupled fixedly or movably to the shaft portion; and a suction catheter movably accommodating the shaft portion and being provided with a suction lumen for making a suction force act, wherein the suction catheter includes a base member having a tubular shape, and a distal side tubular portion having a tubular shape and located at a distal side of the base member, the distal side tubular portion inclining toward a predetermined direction with respect to a central axis of the base member, the distal side tubular portion includes a distal side opening configured to allow entry of the proximal coupling portion at a distal end, and a suction port opening at a side surface on the proximal side of the distal side opening, an opening area of the suction port is larger than a cross-sectional area of the suction lumen, and the suction port opens toward a direction opposite to a direction of inclination of the distal side tubular portion with respect to the base member.

In accordance with an exemplary embodiment, a treatment method is disclosed for trapping and suctioning an object in a biological lumen by using the suction system described above, the treatment method including: a step of indwelling the expansion portion coupled to the shaft portion in a biological lumen; a step of causing an object generated at the lesion area to drop off the lesion area in the biological lumen; a step of moving the suction catheter to the distal side along the shaft portion to cause the proximal side coupling portion to be attached or inserted into the distal side opening; and a step of suctioning the object collected in the expansion portion by the suction catheter.

According to the suction catheter, the suction system and the treatment method configured as described above, the opening area of the opening of the suction catheter, which is capable of suctioning, is larger than a cross-sectional area of the suction lumen. Therefore, suction over a wide range and suction of a larger object are enabled, and thus an effective suction of the object can be achieved. In addition, suction is performed with the distal side opening of the suction catheter in contact with the device configured to collect the object in the biological lumen, and thus a stable procedure not depending on the operator is provided.

In accordance with an exemplary embodiment, a method is disclosed for suctioning an object in a blood vessel, the method comprising: inserting an expansion portion connected to a shaft portion on a distal portion of the shaft portion into the blood vessel; expanding the expansion portion in the blood vessel; inserting a suction catheter along the shaft portion into the blood vessel; reciprocating at least the expansion portion or the suction catheter relative to each other along an axial axis of the shaft portion; and suctioning the object with the suction catheter.

In accordance with an another exemplary embodiment, a method is disclosed for suctioning an object in a blood vessel, the method comprising: inserting an expansion portion connected a shaft portion on a distal portion of the shaft portion into the blood vessel; expanding the expansion portion in the blood vessel; inserting a suction catheter along the shaft portion into the blood vessel; moving a proximal side coupling portion of the expansion portion or the suction catheter along an axial axis of the shaft portion relative to each other along an axial axis of the shaft portion; breaking the object by the proximal side coupling portion and the suction catheter; and suctioning the object by the suction catheter.

In accordance with an exemplary embodiment, a method is disclosed for suctioning an object in a blood vessel, the method comprising: inserting an expansion portion connected a shaft portion on a distal portion of the shaft portion into the blood vessel; expanding the expansion portion in the blood vessel; inserting a suction catheter along the shaft portion into the blood vessel; inserting a breaking device into the blood vessel along the shaft portion; breaking the object by the breaking device; moving a proximal side coupling portion of the expansion portion or the suction catheter along an axial axis of the shaft portion relative to each other along an axial axis of the shaft portion; suctioning a broken object by the suction catheter; and removing the suction catheter and the expansion portion from the blood vessel.

BRIEF DESCRIPTION OF THE DRAWINGS

FIG. 1 is a plan view illustrating a suction system according to a first exemplary embodiment.

FIG. 2 is a plan view illustrating a state in which an expanding tool, a pressing shaft, and a sheath of the suction system are assembled according to the first exemplary embodiment.

FIGS. 3A and 3B illustrate plan views of an expansion portion of the expanding tool, in which FIG. 3A illustrates a state in which the expansion portion is expanded, and FIG. 3B illustrates a state in which the expansion portion is contracted.

FIG. 4 is enlarged cross-sectional views illustrating a proximal side coupling portion and a distal side coupling portion.

FIGS. 9A and 9B illustrate drawings of a distal portion of a suction catheter, in which FIG. 9A is a plan view and FIG. 9B is a cross-sectional view.

FIGS. 11A and 11B illustrate cross-sectional views of a state in a blood vessel, in which FIG. 11A illustrates a state in which the expansion portion is inserted into the blood vessel, and FIG. 11B illustrates a state in which the expansion portion is expanded in the blood vessel.

FIGS. 12A and 12B illustrate cross-sectional views of a state in a blood vessel, in which FIG. 12A illustrates a state in which the expansion portion is indwelled in the blood vessel in a folded state, and FIG. 12B illustrates a state in which the breaking device is inserted into the blood vessel.

FIGS. 15A and 15B illustrate cross-sectional views of a state in a blood vessel, in which FIG. 15A illustrates a state in which a breaking member of the breaking device is expanded and FIG. 15B illustrates a state in which blood clots are broken by the expanded breaking member.

DETAILED DESCRIPTION

Figure 5:
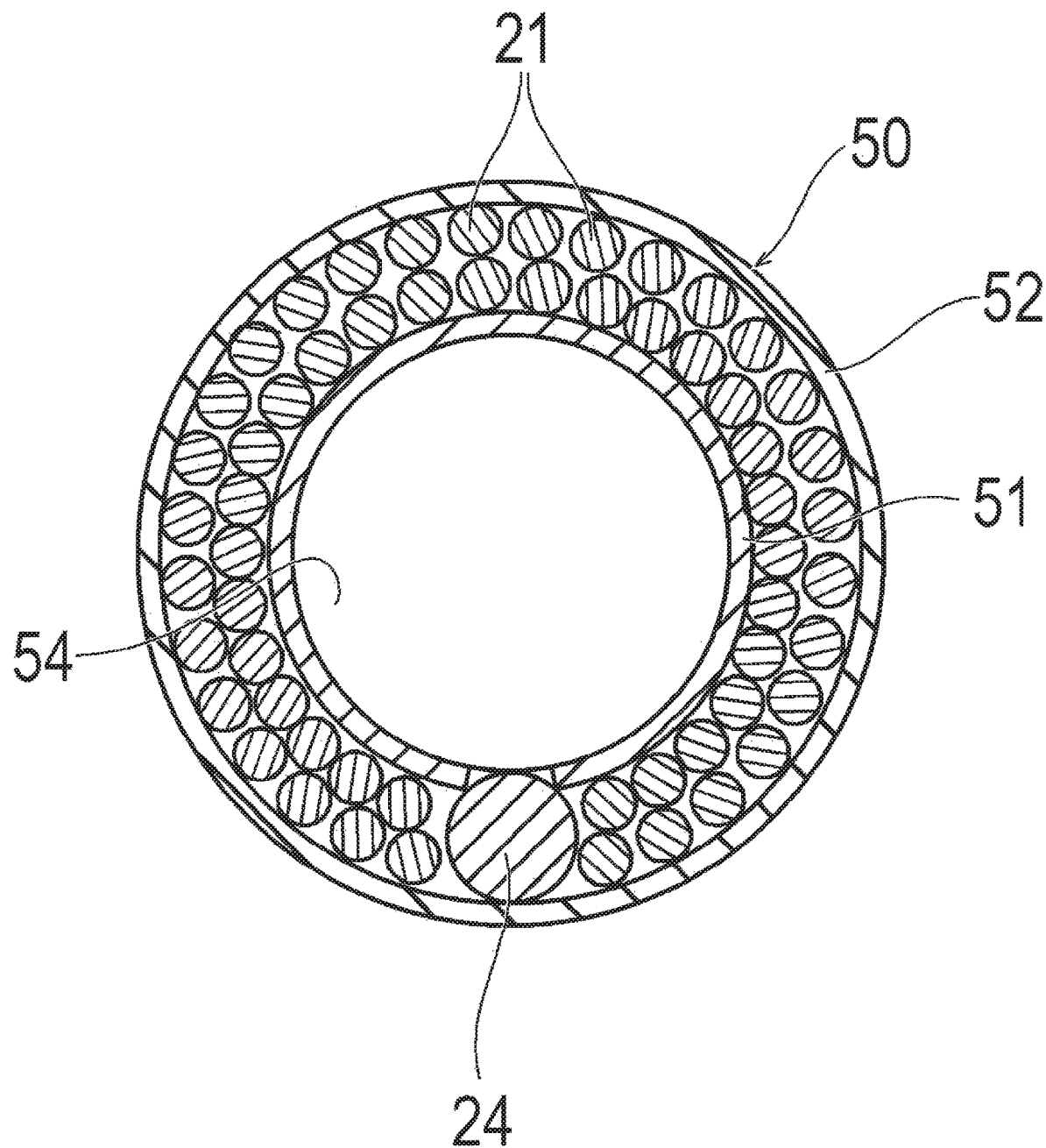
FIG. 5 is a cross-sectional view taken along a line V-V in FIG. 4.

Embodiments of the disclosure will be described with reference to the drawings below. Note that dimensional ratios of the drawings may be exaggerated and thus may be different from actual ratios for the sake of convenience of description.

A suction system 1 according to exemplary embodiment of the present disclosure is used for preventing or reducing part of a flow in a blood vessel for suctioning and removing objects such as blood clots or plaques in the blood vessel. Note that a side of a device which is inserted into blood vessels is referred to as "distal side" and a hand-side to be operated is referred to as "proximal side" in this specification. The objects to be removed are not particularly limited to the blood clots and the plaques and may be any objects that may be present in a biological lumen. In this specification, a source side of a blood flow in a blood vessel is referred to as "upstream side" (i.e., proximal) and a side toward which the blood flows is referred to as "downstream side" (i.e., distal).

First Embodiment

The suction system 1 according to a first exemplary embodiment of the present disclosure includes an expanding tool 10 configured to limit the flow of the blood in the blood vessel, a suction catheter 30 configured to be capable of accommodating the expanding tool 10, and a pressing shaft 40 configured to be used for pushing out the expanding tool 10 from the suction catheter 30 as illustrated in FIGS. 1 and 2. Note that limiting the blood flow means partly blocking a cross section vertical to an axis of the blood vessel or reducing the flow rate of the blood by reducing the cross section.

In accordance with an exemplary embodiment, the expanding tool 10 includes an expansion portion 20, which is a net-type cylindrical member provided with a plurality of gaps (or spaces) 21A, a closing member 70 disposed in an inner peripheral surface of the expansion portion 20, a shaft portion 24 having an elongated shape to be coupled to the expansion portion 20, and an auxiliary expansion portion 80 provided on a distal side of the expansion portion 20 as illustrated in FIGS. 3A, 3B, and 4.

The shaft portion 24 is an elongated wire penetrating from a hand-side (proximal side) through the expansion portion 20 to the auxiliary expansion portion 80 as illustrated in FIGS. 1, 3A, and 3B.

The shaft portion 24 material is not particularly limited, but stainless steel or a shape-memory alloy, for example, may be preferably used.

The expansion portion 20 is a portion functioning as a filter for trapping the blood clots. As illustrated in FIGS. 3A and 3B, the expansion portion 20 includes a plurality of flexibly deformable wire members 21 braided into a net shape so as to constitute a cylindrical member having the gaps 21A, a distal side coupling portion 50 fixedly coupled to the shaft portion 24, and a proximal side coupling portion 60 slidably coupled to the shaft portion 24. The plurality of the wire members 21 include the gaps 21A between the wire members 21 by being braided. The cylindrical member made of the plurality of wire members 21 includes the film-type closing member 70 fixed to an inner peripheral surface of a proximal portion. Therefore, in a natural state in which no external force is applied, an outer diameter of a proximal portion of the expansion portion 20 is larger than an outer diameter of a distal portion due to an effect of the closing member 70. In accordance with an exemplary embodiment, the distal portion and the proximal portion of the expansion portion 20 have an asymmetric structure. In accordance with an exemplary embodiment, the portion where the closing member 70 of the expansion portion 20 is not fixed is easier to deform than the portion where the closing member 70 of the expansion portion 20 is fixed. Note that the expansion portion 20 in accordance with an embodiment may have a structure in which the distal portion and the proximal portion have a symmetric structure.

The distal side coupling portion 50 includes an inner tube 51 located inside the wire members 21 and an outer tube 52 located outside the wire members 21 as illustrated in FIGS. 4 and 5. Distal ends of the wire members 21 and the shaft portion 24 are interposed and fixed between the inner tube 51 and the outer tube 52. The inner surface side of the inner tube 51 corresponds to a guide wire lumen 54 that allows insertion of the guide wire.

Figure 6:
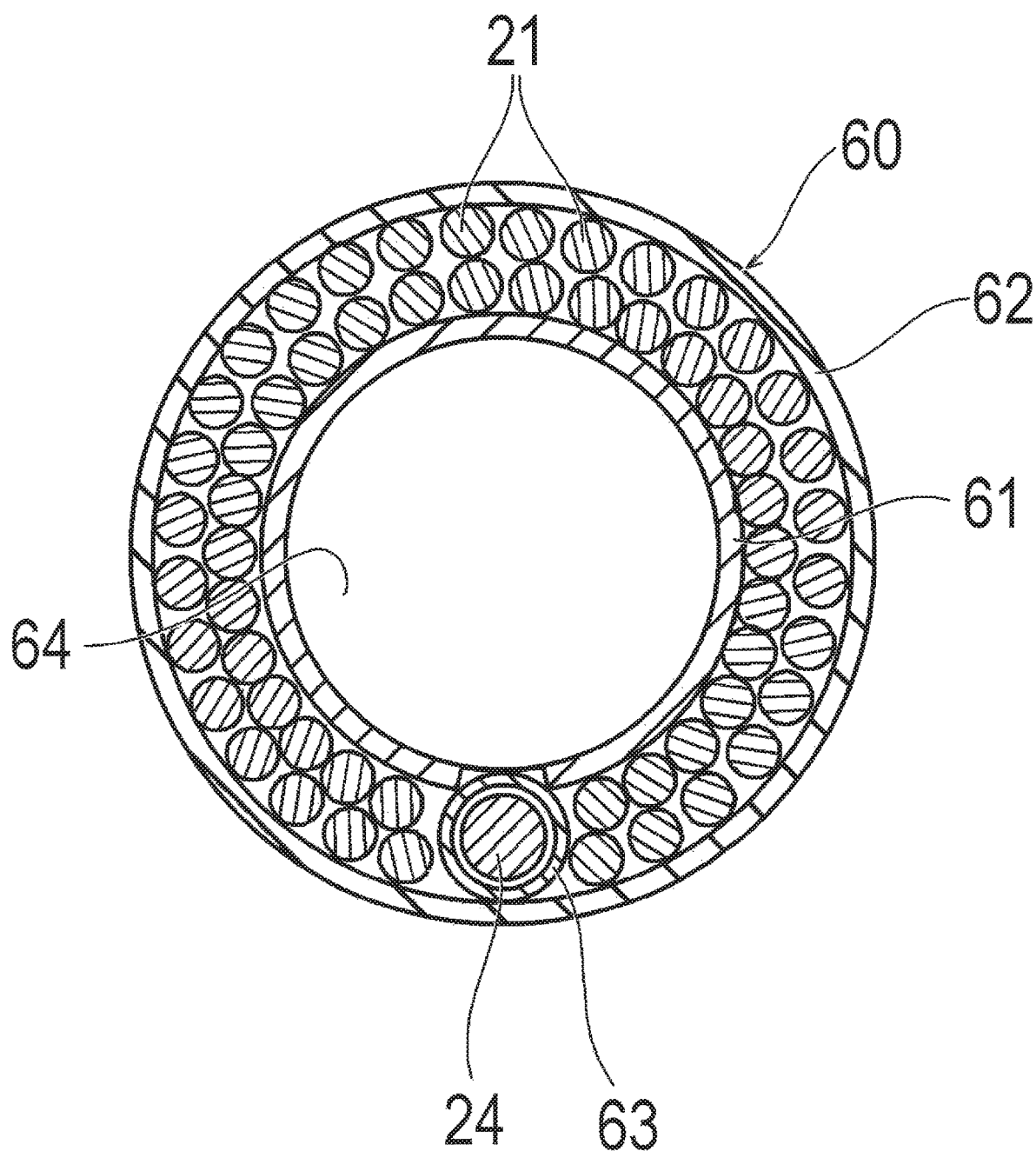
FIG. 6 is a cross-sectional view taken along a line VI-VI in FIG. 4.

As illustrated in FIGS. 4 and 6, the proximal side coupling portion 60 includes an inner tube 61 located inside the wire members 21, an outer tube 62 located outside the inner tube 61, and a guiding tubular member 63 to be interposed (i.e., inserted) between the inner tube 61 and the outer tube 62. The end portions of the wire members 21 on the proximal side and the guiding tubular member 63 are interposed and fixed between the inner tube 61 and the outer tube 62. The shaft portion 24 is slidably disposed inside the guiding tubular member 63. Therefore, the proximal side coupling portion 60 is movable in an axial direction along the shaft portion 24. The inner surface side of the inner tube 61 corresponds to a guide wire lumen 64 which allows insertion of the guide wire. In accordance with an exemplary embodiment, a cross-sectional area vertical to the axial direction of the proximal side coupling portion 60 is larger than a cross-sectional area vertical to the axial direction of the shaft portion 24.

In the natural state in which no external force is applied, the expansion portion 20 assumes an expanded state (see FIG. 3A) enlarged in diameter by its own resilient force (restoration force) of the wire members 21. When the expansion portion 20 assumes an expanded state, the proximal side coupling portion 60 slides to the distal side with respect to the shaft portion 24 and moves toward the distal side coupling portion 50. The expansion portion 20 assumes a contracted state (see FIG. 3B) in which the outer diameter is resiliently reduced by being accommodated in the suction catheter 30 (see FIGS. 1 and 2). When the expansion portion 20 assumes a contracted state, the proximal side coupling portion 60 slides to the proximal side with respect to the shaft portion 24 and moves away from the distal side coupling portion 50. The outer diameter of the braided expansion portion 20 is configured to be variable by varying distance between the proximal side coupling portion 60 and the distal side coupling portion 50.

In accordance with an exemplary embodiment, the expansion portion 20 includes a proximal side tapered portion 20A located on the proximal side, a distal side tapered portion 20C located on the distal side, and a center portion 20B located between the proximal side tapered portion 20A and the distal side tapered portion 20C. In accordance with an exemplary embodiment, the proximal side tapered portion 20A is gradually increased in inner and outer diameters from the proximal side coupling portion 60 to the distal side in an inverted tapered shape. The distal side tapered portion 20C is gradually increased in inner and outer diameters from the distal side coupling portion 50 to the proximal side in an inverted tapered shape. The center portion 20B is gradually reduced in inner and outer diameters from the proximal side tapered portion 20A to the distal side tapered portion 20C in a tapered shape. The center portion 20B is a portion where the expansion portion 20 comes into contact (i.e., indwells) with an intravascular wall when being expanded. Note that the portion of the expansion portion 20 coming into contact with the intravascular wall when being expanded may be the proximal side tapered portion 20A or may be the distal side tapered portion 20C.

The number of the wire members 21 is not particularly limited, but may be four to seventy-two, for example. Conditions of the braiding of the wire members 21 are not particularly limited. The outer diameter of the wire members 21 may be selectable appropriately depending on materials of the wire members 21 or applications of expansion portion 20 and, for example, may be 20 μm to 300 μm.

The material of the wire members 21 is preferably one of flexible materials and, for example, shape-memory alloy which is provided with a shape-memory effect and superelasticity by heat treatment, stainless steel, tantalum (Ta), titanium (Ti), platinum (Pt), gold (Au), and tungsten (W), polyolefin such as polyethylene and polypropylene, polyester such as polyamide and polyethylene terephthalate, fluorinated polymers such as tetrafluoroethylene-ethylene copolymer (ETFE), polyether ether ketone (PEEK), and polyimide are preferably used. As the shape-memory alloy, Ni—Ti based, Cu—Al—Ni based, Cu—Zn—Al based alloys, and a combination the shape-memory alloy, Ni—Ti based, Cu—Al—Ni based, and Cu—Zn—Al based alloys are preferably used. Examples of a structure combined with a plurality of materials of the wire members 21 can include, for example, a structure such as a core wire made of Pt covered with Ni—Ti alloy and a structure of a core wire made of Ni—Ti covered with gold plating for providing imaging property.

The outer diameters of the outer tubes 52 and 62 are not particularly limited. The outer diameters of the outer tubes 52 and 62 can be, for example, between 0.3 mm and 3.0 mm. The inner diameters of the inner tubes 51 and 61 are not particularly limited. The inner diameters of the inner tubes 51 and 61 can be, for example, between 0.1 mm and 2.0 mm.

Materials of the inner tubes 51 and 61 and the outer tubes 52 and 62 are not particularly limited. For example, stainless steel may preferably be used as the material for the inner tubes 51 and 61 and the outer tubes 52 and 62.

In accordance with an exemplary embodiment, the maximum outer diameter of the expansion portion 20 in an expanded state may be selected depending on the inner diameter of the blood vessel to be applied as appropriate. The maximum outer diameter of the expansion portion 20 can be, for example, between 1 mm to 40 mm. The outer diameter of the expansion portion 20 in the contracted state is selectable appropriately depending on the inner diameter of the blood vessel to be applied. The outer diameter of the expansion portion 20 can be, for example, between 0.3 mm to 4.0 mm. The length of the expansion portion 20 in the axial direction in the expanded state is selectable appropriately depending on the blood vessel to be applied. The length of the expansion portion 20 in the axial direction in the expanded state can be, for example, between 20 mm and 150 mm.

Figure 7:
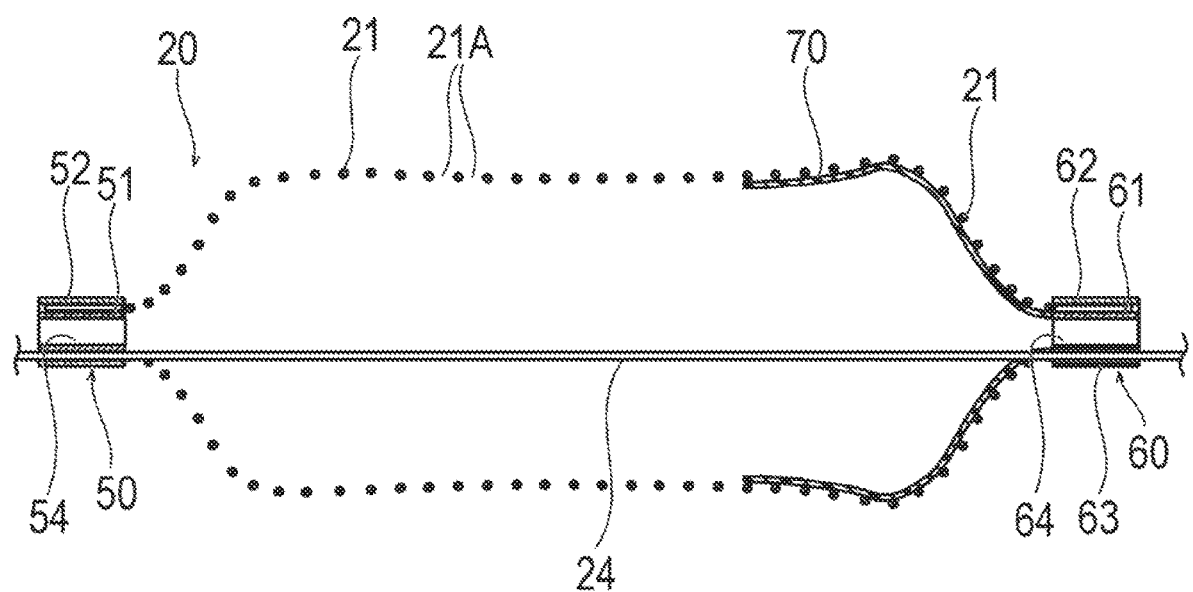
FIG. 7 is a cross-sectional view illustrating an expansion portion and a closing member in a natural state.

In accordance with an exemplary embodiment, the closing member 70 is a thin-film shaped member fixed on an inner peripheral surface of the expansion portion 20 on the proximal side as illustrated in FIG. 7. The closing member 70 closes the gaps 21A of the expansion portion 20. The closing member 70 is flexibly deformable in conformance with the expansion portion 20. The closing member 70 is preferably disposed in a range of half or less of the axial length of the expansion portion 20 in the expanded state to avoid complete blockage of the blood vessel in a folded state described later (see FIG. 8), but is not limited thereto. The thickness of the closing member 70 is not particularly limited and, for example, may be between 0.01 mm to 0.2 mm.

The closing member 70 material is preferably a flexible material. For example, preferably the closing member 70 material is urethane, natural rubber, and/or silicone resin. The closing member 70 may be a member having air permeability and liquid permeability. For example, the closing member 70 is fixed to the expansion portion 20 by dipping. Note that the closing member 70 may be provided on an outer peripheral surface side of the expansion portion 20. The closing member 70 may be provided between an inner peripheral surface and an outer peripheral surface of the expansion portion 20, that is, within a range of spaces of the gaps 21A. Note that the closing member 70 may have any configuration as long as the air permeability or the liquid permeability of the gaps 21A can be limited and deformation with the expansion portion 20 is allowed.

Figure 8:
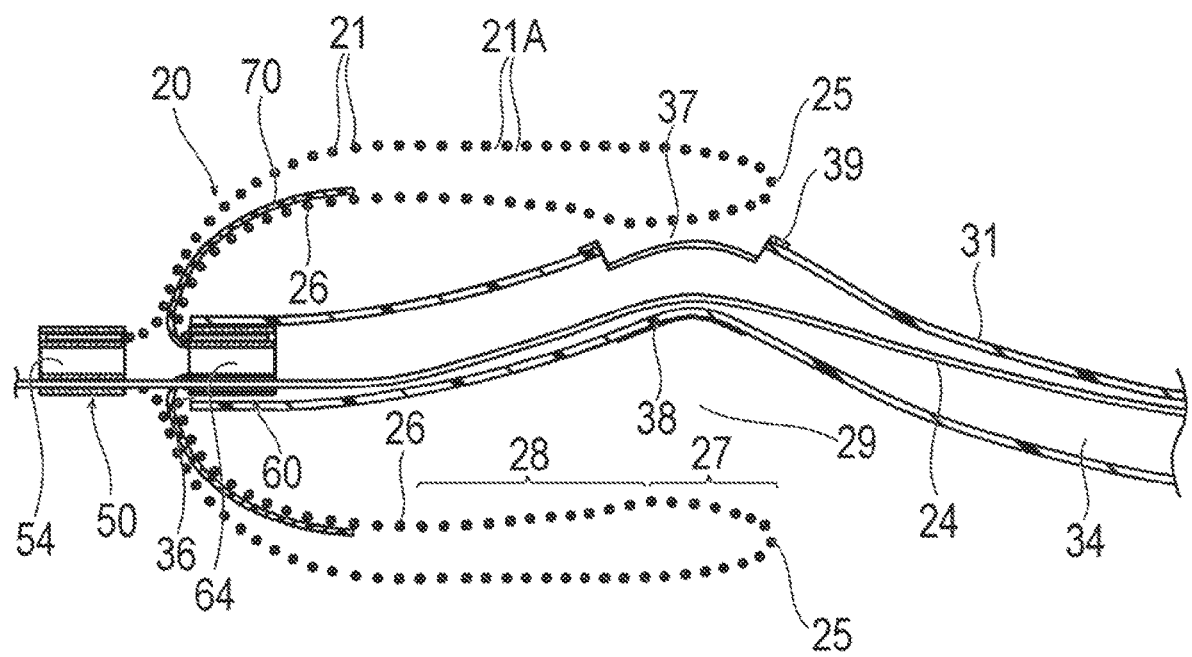
FIG. 8 is a cross-sectional view illustrating the expansion portion and the closing member in a folded state.
Figure 9A:
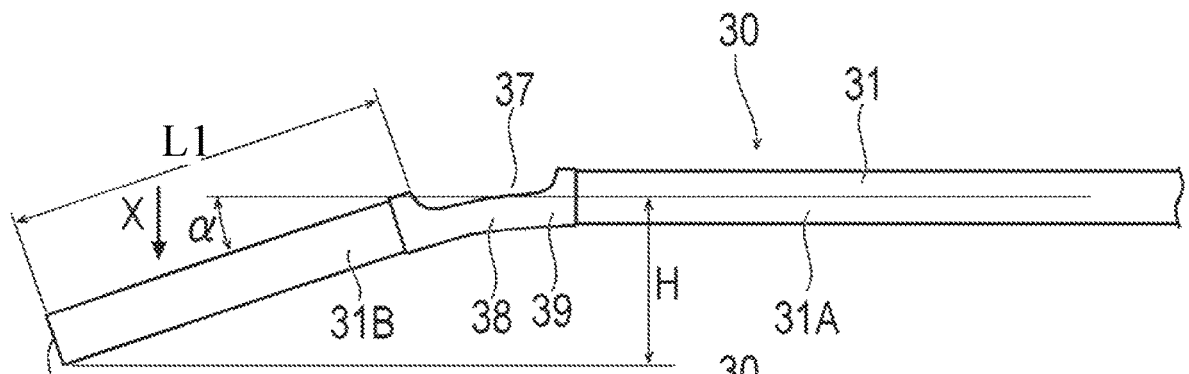
Figure 9B:
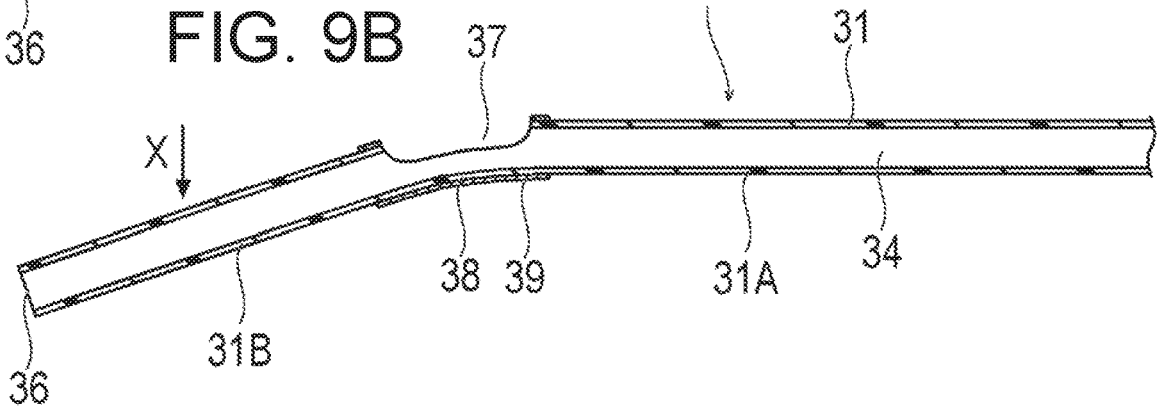

In accordance with an exemplary embodiment, the expansion portion 20 assumes a folded state, which is a state of being folded in the axial direction, by the proximal side coupling portion 60 slid toward the distal side with respect to the shaft portion 24 to a position near the distal side coupling portion 50 and placed in an interior of the expansion portion 20 as illustrated in FIG. 8. The interior of the expansion portion 20 is an area surrounded by an inner surface of the expansion portion 20 and the central axis. The inner surface of the expansion portion 20 means an inner surface of a cylindrical member formed by the braided wire members 21. In the folded state, the expansion portion 20 includes a folded portion 25 which constitutes an end portion on the proximal side in the axial direction by being folded, and a folded inner portion 26 located inside in a radial direction by being folded. The closing member 70 is disposed on a side where the folded inner portion 26 rather than the folded portion 25 is provided, that is, on the side closer to the proximal side coupling portion 60 (center side). In accordance with an exemplary embodiment, the closing member 70 is disposed only partly within a range from the folded portion 25 to the folded inner portion 26. Therefore, the closing member 70 is disposed on part of the expansion portion 20 when viewed in the axial direction of the shaft portion 24 in a folded state. In the folded state, the maximum outer diameter of the closing member 70 is smaller than the maximum outer diameter of the expansion portion 20. Therefore, the closing member 70 blocks the blood vessel to be applied only partly, but not completely.

In the folded state, the distance between the proximal side coupling portion 60 and the distal side coupling portion 50 is set as appropriate. The distance between the proximal side coupling portion 60 and the distal side coupling portion 50 may be different depending on the inner diameter of the blood vessel to be applied. In accordance with an exemplary embodiment, the closing member 70 may or may not come into contact with the inner peripheral surface of the distal portion of the expansion portion 20. When the expansion portion 20 assumes the folded state from the expanded state, at least part of the closing member 70 is reversed (i.e., extending towards the hand side or proximal side and on outer portion of the proximal side couple portion 60). In order that the closing member 70 is restored from an original state (see FIG. 7), a certain degree of force may be required. Therefore, in accordance with an exemplary embodiment, the expansion portion 20 and the closing member 70 in the folded state have a shape stability to a certain degree (i.e., a force is necessary to restore the closing member from the folded state to the original state).

In the folded state, inner peripheral surfaces of the folded portion 25 of the expansion portion 20 in an overlapped state do not come into contact with each other. Therefore, the expansion portion 20 is folded back at the folded portion 25 in a separated state. Note that the inner surface of the expansion portion 20 means an inner surface of a cylindrical member formed by braided wire members 21, and the outer surface of the expansion portion 20 means an outer surface of the cylindrical member.

In the folded state, the expansion portion 20 includes a reducing portion 27 reduced in diameter once from the folded portion 25 toward the proximal side coupling portion 60 located inside the expansion portion 20 and an increasing portion 28 increasing in diameter from the reducing portion 27. Accordingly, in the folded state, an internal space 29 depressed in the axial direction of the expansion portion 20 is widened in an inner part than an entrance part. The increasing portion 28 needs to pass through inside the reducing portion 27 for the expansion portion 20 returning back to the original state (see FIG. 7) from the folded state, and thus a certain degree of force is required. Therefore, the expansion portion 20 in the folded state has a shape stability to a certain degree.

In accordance with an exemplary embodiment, the expansion portion 20 has a larger diameter at the proximal portion than the distal portion, and thus the internal space 29 is increased in the folded state. Therefore, a large space may be allocated for accommodating the object such as blood clots.

In accordance with an exemplary embodiment, the suction catheter 30 includes a sheath tubular member 31, a hub 32, and an anti-kink protector 33 as illustrated in FIGS. 1, 2, 9A, and 9B. The suction catheter 30 is capable of accommodating the expanding tool 10 and suctioning or sucking (i.e., draw by suction) and removing the blood clots in the blood vessel to outside the body.

In accordance with an exemplary embodiment, the sheath tubular member 31 is capable of accommodating the expanding tool 10, and is provided with a suction lumen 34 capable of making a suction force act from the proximal side. The sheath tubular member 31 includes a distal side opening 36 from which the suction lumen 34 opens at a distal end. The sheath tubular member 31 includes a suction port 37 from which the suction lumen 34 opens on a side surface of the proximal side than the distal side opening 36. The sheath tubular member 31 includes a linear base member 31A located on the proximal side, a bent portion 38 located on the distal side of the base member 31A, and a distal side tubular portion 31B located on the distal side of the bent portion 38. The bent portion 38 is curved or bent. Therefore, the distal side tubular portion 31B is inclined in a predetermined direction X with respect to the central axis of the base member 31A. In accordance with an exemplary embodiment, an angle $\alpha$ of inclination of the distal side tubular portion 31B with respect to the base member 31A is not particularly limited. For example, the angle $\alpha$ can range from 10 degrees to 90 degrees, more preferably from 30 degrees to 80 degrees, and more preferably, from 50 degrees to 70 degrees. The suction port 37 is opening toward a direction opposite from the direction X in which the distal side tubular portion 31B inclines with respect to the base member 31A. The suction port 37 is provided at the bent portion 38. Note that the position where the suction port 37 is provided does not have to be the opposite side from the direction X of the bent portion 38 and may not be at the bent portion 38. In accordance with an exemplary embodiment, the sheath tubular member 31 includes a reinforcing portion 39 configured to reinforce a portion where the suction port 37 is provided. The reinforcing portion 39 is provided in a range including the suction port 37 of the sheath tubular member 31. Therefore, the reinforcing portion 39 constitutes an edge portion of the suction port 37. In accordance with an exemplary embodiment, the reinforcing portion 39 can help prevent or reduce the sheath tubular member 31, which is lowered in rigidity by the provision of the suction port 37, from being bent or collapsed. Thus, the reinforcing portion 39 can help prevent the operability of the suction catheter 30 from being lowered and the suction force of the suction catheter 30 can be appropriately maintained.

In accordance with an exemplary embodiment, the distal side opening 36 is capable of accommodating and retaining the proximal side coupling portion 60 located on the proximal side of the expansion portion 20 in an expanded state as illustrated in FIG. 8. A distance L1 (see FIG. 9A) from the distal side opening 36 of the suction port 37 is preferably equal to or larger than an axial length L2 (see FIGS. 3A and 3B) of the proximal side coupling portion 60. Accordingly, the proximal side coupling portion 60 inserted into the suction lumen 34 from the distal side opening 36 does not reach the suction port 37 and thus does not interfere with the suction port 37. In accordance with an exemplary embodiment, the inner diameter of the suction lumen 34 is larger than the outer diameter of the proximal side coupling portion 60 so as to allow the proximal side coupling portion 60 to slide in the axial direction and in a rotational direction within the suction lumen 34. In accordance with an exemplary embodiment, a clearance between the inner peripheral surface of the suction lumen 34 and an outer peripheral surface of the proximal side coupling portion 60 when the proximal side coupling portion 60 is inserted into the suction lumen 34 is not particularly limited. For example, the clearance between the inner peripheral surface of the suction lumen 34 and the outer peripheral surface of the proximal side coupling portion 60 can range from 0.1 mm to 1 mm, more preferably from 0.2 mm to 0.6 mm, and further preferably from 0.25 mm to 0.4 mm. When the clearance is too small, the proximal side coupling portion 60 cannot slide within the suction lumen 34. When the clearance is too large, the proximal side coupling portion 60 cannot block the suction lumen 34 adequately, and thus concentration of the suction force to the suction port 37 becomes difficult.

In accordance with an exemplary embodiment, the cross-sectional area orthogonal to the axial direction of the suction lumen 34 located at the distal side opening 36 is larger than the cross-sectional area orthogonal to the axial direction of the proximal side coupling portion 60. The cross-sectional area orthogonal to the axial direction of the proximal side coupling portion 60 is larger than the cross-sectional area orthogonal to the axial direction of the shaft portion 24. Therefore, the clearance (gap) maintained in an interior of the distal side opening 36 is smaller in a case where the proximal side coupling portion 60 attaches or enters the distal side opening 36 than a case where the distal side opening 36 is disposed along the shaft portion 24. Therefore, positional displacement in the radial direction of the suction catheter 30 with respect to the shaft portion 24 or the proximal side coupling portion 60 is relatively small, and hence an object may be suctioned stably through the suction port 37.

In accordance with an exemplary embodiment, an opening area (a surface area on the side surface of the sheath tubular member 31) of the suction port 37 is larger than the cross-sectional area on a cross section orthogonal to the central axis of the suction lumen 34. In accordance with an exemplary embodiment, the suction port 37, being provided on the side surface of the sheath tubular member 31, may be formed to be elongated in the axial direction and may be formed to have a larger cross-sectional area than the cross-sectional area of the suction lumen 34.

With the expansion portion 20 in the folded state, the entire part or part of the suction port 37 in a case where the proximal side coupling portion 60 is inserted into the distal side opening 36 is preferably located on the distal side of the folded portion 25. With the expansion portion 20 in the folded state, a portion where the closing member 70 of the folded portion 25 or the folded inner portion 26 are not provided is preferably located in a direction of opening of the suction port 37 when the proximal side coupling portion 60 is inserted into the distal side opening 36 (a direction orthogonal to the axial direction of a sheath tubular member 31). Accordingly, the expansion portion 20 that functions as a filter is located in front (distally) of the suction port 37. Therefore, blood clots adhering to the expansion portion 20 may be suctioned efficiently from the suction port 37. Note that the suction port 37 when the proximal side coupling portion 60 is inserted into the distal side opening 36 may be located on the proximal side of the folded portion 25 in the folded state. Therefore, the expansion portion 20 does not have to be present in the direction of opening of the suction port 37.

In accordance with an exemplary embodiment, a separated distance H (see FIG. 9A) from the central axis of the sheath tubular member 31 on the proximal side of the bent portion 38 to the distal end portion of the sheath tubular member 31 is equal to or larger than a radius of the folded portion 25 in the folded state (the radius of the entrance port of the internal space 29). Accordingly, the sheath tubular member 31 may be brought into contact with the expansion portion 20 by rotating the sheath tubular member 31. Therefore, blood clots can be rather easily separated from the expansion portion 20 due to a rotational force of the sheath tubular member 31, direct contact with blood clots adhering to the expansion portion 20 of the sheath tubular member 31, or an impact force transferred to the expansion portion 20. Therefore, the blood clots may be suctioned rather efficiently from the suction port 37 even in a flow. When the sheath tubular member 31 comes into contact with the expansion portion 20, a bending position of the sheath tubular member 31 may vary in conformance with the shape of the expansion portion 20. When the sheath tubular member 31 comes into contact with the expansion portion 20, the expansion portion 20 may be deformed and a position of the proximal side coupling portion 60 may vary.

In a state in which the proximal side coupling portion 60 is inserted into the distal side opening 36, the closing member 70 is located on the distal side of a portion where the distal side opening 36 of the suction catheter 30 is provided. Since the closing member 70 limits the flow in the blood vessel, in the vicinity of the distal side opening 36 of the suction catheter 30, the flow of the blood vessel is limited and blood clots float without adhering to the expansion portion 20. Therefore, necessity of making a strong suction force act on this area can be relatively low. Therefore, the distal side opening 36 is blocked by the proximal side coupling portion 60, and instead, the suction force is concentrated on the suction port 37 where a strong suction force can be required.

Figure 18:
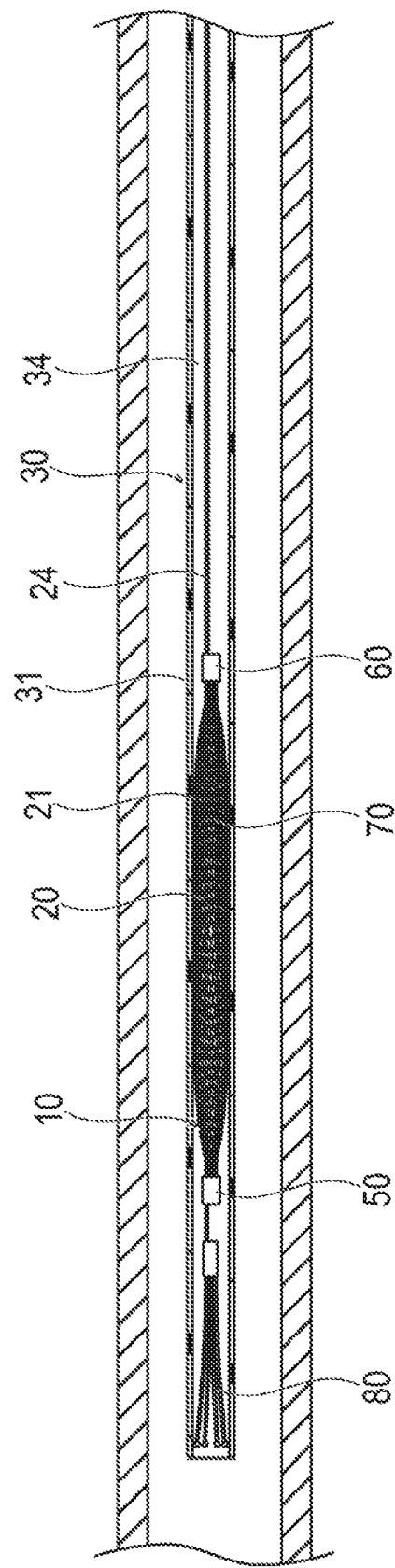
FIG. 18 illustrates a state in which the expansion portion is accommodated in the suction catheter.

In accordance with an exemplary embodiment, the hub 32 is fixed to an end portion on the proximal side of the sheath tubular member 31. The hub 32 is provided with a hub opening 35 in communication with the suction lumen 34 as illustrated in FIGS. 1, 2, and 18. The hub opening 35 allows coupling of a Y connector 190 provided with a side tube 191. By coupling the Y connector 190, a syringe 180 configured to generate a negative pressure may be brought into communication with the Y connector 190 in a state in which an elongated device (for example, the shaft portion 24) is inserted into the hub opening 35. By connecting the syringe 180 to the side tube 191 of the Y connector 190, a thrombolytic agent may be injected into a lumen of the sheath tubular member 31 from the syringe 180. In accordance with an exemplary embodiment, the anti-kink protector 33 is a flexible member configured to cover a coupling portion between the sheath tubular member 31 and the hub 32. The anti-kink protector 33 can help restrict kinking of the sheath tubular member 31.

The sheath tubular member 31 material is not particularly limited, for example, polyolefin such as polyethylene, polypropylene, ethylene-propylene copolymer, ethylene-vinyl acetate copolymer, polyvinyl chloride, polystyrene, polyamide, polyimide, or a combination polyethylene, polypropylene, ethylene-propylene copolymer, ethylene-vinyl acetate copolymer, polyvinyl chloride, polystyrene, polyamide, and polyimide may be preferably used. In accordance with an exemplary embodiment, the sheath tubular member 31 may be made of a plurality of materials, or a reinforcing member such wires may be embedded.

The reinforcing portion 39 material is preferably harder than the material of the sheath tubular member 31 and, for example, stainless steel may be preferably used as the reinforcing portion 39 material.

A pressing shaft 40 is a tubular member that can be accommodated in the suction lumen 34 of the suction catheter 30. The pressing shaft 40 includes a push-out lumen 41 that allows insertion of the shaft portion 24 of the expanding tool 10 in the interior of push-out lumen 41. In accordance with an exemplary embodiment, the inner diameter of the push-out lumen 41 is smaller than the outer diameter of the proximal side coupling portion 60 of the expanding tool 10. Therefore, the proximal side coupling portion 60 cannot enter the push-out lumen 41. Therefore, the proximal side coupling portion 60 may be pushed to the distal side by an end surface of the distal side of the pressing shaft 40.

Subsequently, a breaking device 100 configured to be inserted into the blood vessel to rotate and break blood clots will be described.

Figure 10:
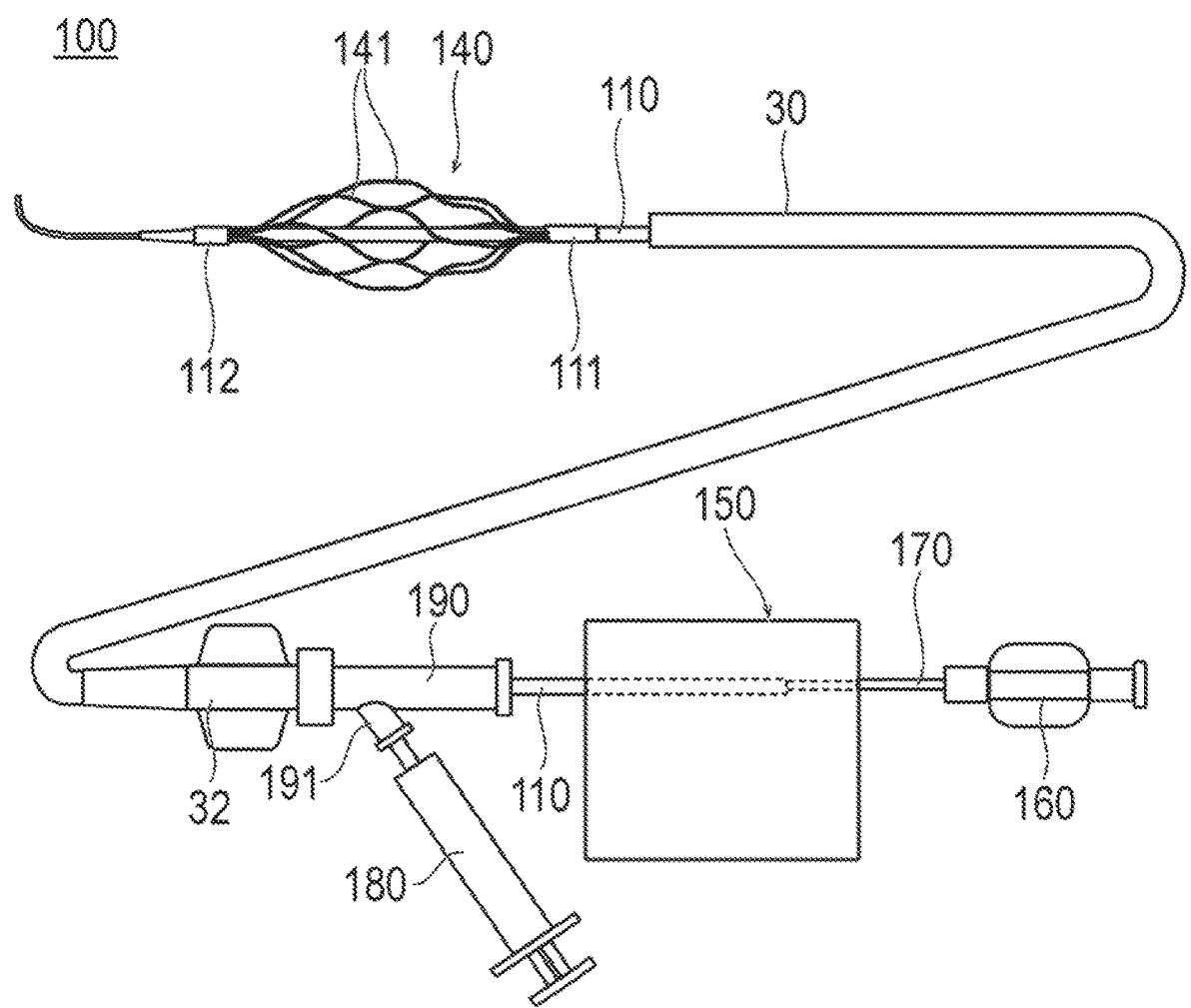
FIG. 10 is a plan view illustrating a breaking device.

The breaking device 100 includes a driving shaft 110 having an elongated shape and configured to be rotationally driven, a slide portion 111 configured to be slidable with respect to the driving shaft 110, and a breaking member 140 rotated by the driving shaft 110 as illustrated in FIG. 10. The breaking device 100 further includes a rotary drive unit 150 provided with a driving source (for example, a motor) to rotate the driving shaft 110, a tubular member 170 for a guide wire configured to allow insertion of the guide wire, and a hub 160 provided at the proximal end portion of the tubular member 170 of the guide wire. The driving shaft 110 may be accommodated in the suction catheter 30 via the Y connector 190.

The proximal end portion of the driving shaft 110 is located at the rotary drive unit 150. In accordance with an exemplary embodiment, the driving shaft 110 is reciprocally movable along a circumferential direction by the rotary drive unit 150. However, the driving shaft 110 is not limited to be configured to reciprocate, but may be configured to rotate in one direction.

The tubular member 170 for the guide wire is provided in a hollow interior of the driving shaft 110 from the distal end portion to the hub 160. The tubular member 170 for the guide wire includes a guide wire lumen configured to allow insertion of the guide wire.

The breaking member 140 is provided at a distal portion of the driving shaft 110. The breaking member 140 includes a plurality of (six in this exemplary embodiment) wires 141. Each of the wires 141 is three-dimensionally curved. Note that the number of the wires 141 is not particularly limited. Each of the wires 141 is twisted in the same circumferential direction along the axial direction of the driving shaft 110. The proximal end portion of each of the wires 141 is fixed to the sliding portion 111 configured to be slidable with respect to the driving shaft 110. The distal end portion of each of the wires 141 is fixed to a fixed portion 112 fixed to the driving shaft 110. Positions for fixation of the respective wires 141 to the fixed portion 112 and the sliding portion 111 are arranged in the circumferential direction. Substantially center portions of the respective curved wires 141 in the axial direction are arranged in the circumferential direction at positions radially away from the driving shaft 110. Accordingly, the breaking member 140 has a uniform bulge in the circumferential direction as a whole. When the driving shaft 110 rotates, the breaking member 140 rotates correspondingly, and thus is capable of breaking blood clots in the blood vessel or rotating the broken blood clots. In accordance with an exemplary embodiment, the breaking member may be a laser cut pipe such as a stent instead of the wires.

The wires 141 that constitute the breaking member 140 are made of metallic thin wires having flexibility. Until the driving shaft 110 is inserted to an intended portion, the breaking member 140 is stored in the interior of the suction catheter 30. When the suction catheter 30 is slid to the proximal side with respect to the driving shaft 110 after the driving shaft 110 is inserted to the intended portion, the breaking member 140 is exposed to outside the suction catheter 30 and expanded. Therefore, the wires 141 are preferably made of a material having a shape-memory property.

Figure 19:
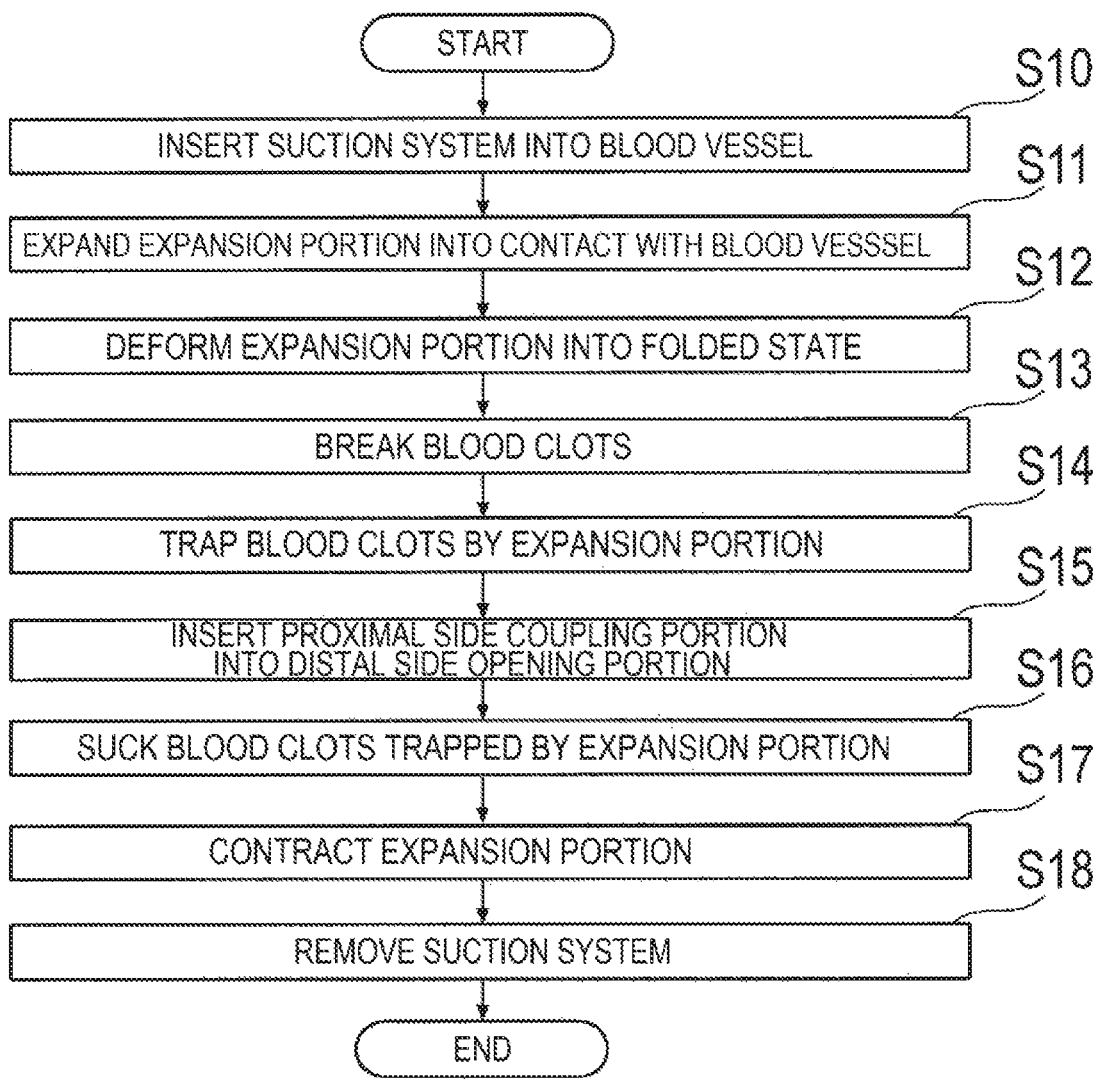
FIG. 19 is a flow chart for explaining a procedure using the suction system.

Next, a method of using the suction system 1 and the breaking device 100 according to the present exemplary embodiment will be described with an example of a case of suctioning and removing blood clots (object) in a blood vessel (biological lumen) with reference to a flow chart in FIG. 19.

First, an introducer sheath (not illustrated) is inserted into the blood vessel percutaneously on an upstream side (proximal side) of blood clots 300 in the blood vessel, and a guide wire 90 is inserted into the blood vessel via the introducer sheath. Next, the guide wire 90 is advanced to reach a distal side of the blood clots 300.

Next, as illustrated in FIG. 2, the suction system 1 with the expanding tool 10 and the pressing shaft 40 accommodated in the suction catheter 30 is prepared. The Y connector 190 is connected to the hub 32 of the suction catheter 30. The expansion portion 20 and an auxiliary expansion portion 80 are disposed at a position closer to the distal end portion of the sheath tubular member 31, and the shape is restricted in a contracted state. The shaft portion 24 passes from the hub opening 35 of the hub 32 through the Y connector 190 and is projected from the proximal side.

Figure 11:
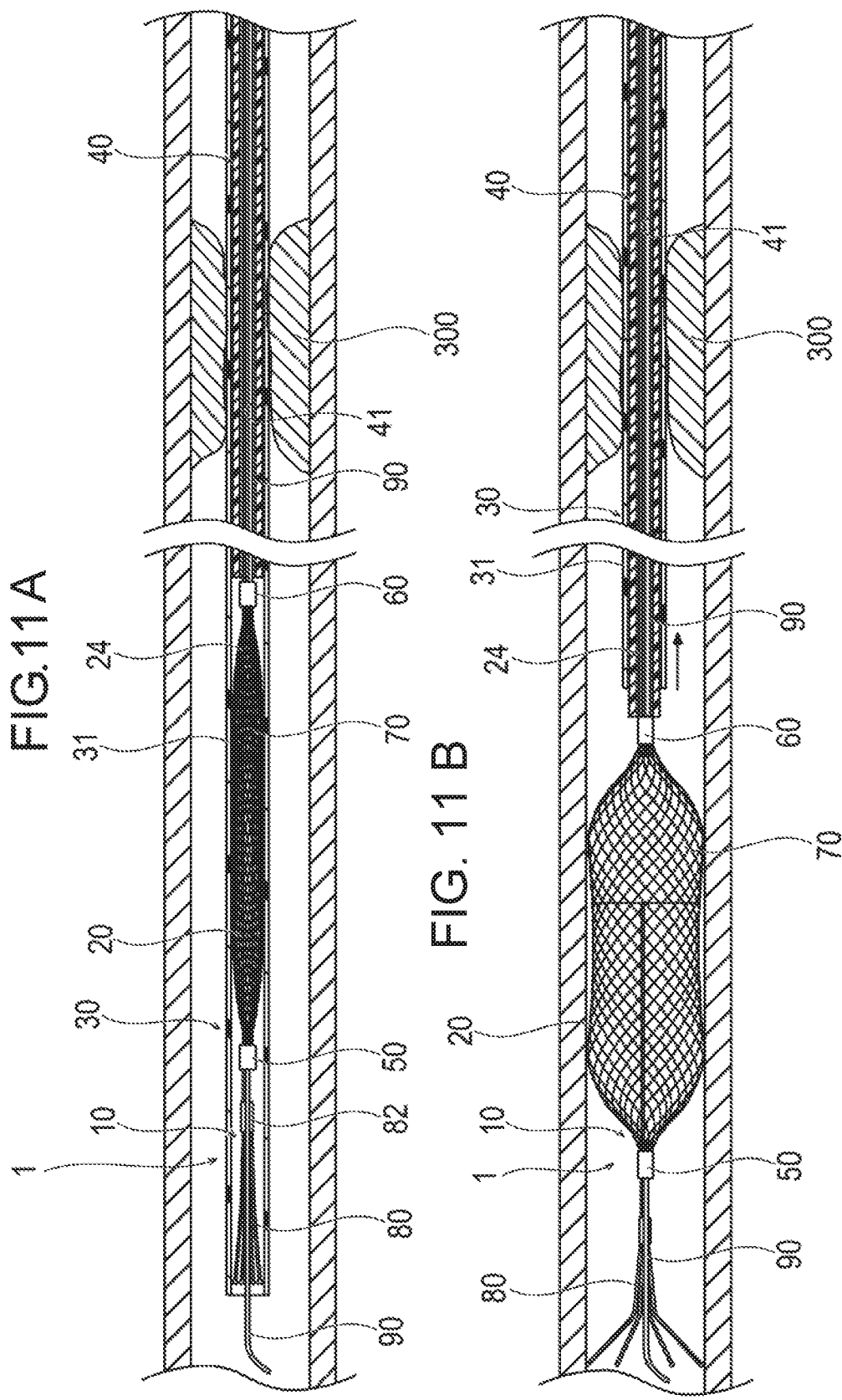

Subsequently, the proximal end portion of the guide wire 90 located outside the body is inserted into the guide wire lumens 54 and 64 (see FIG. 7) of the suction system 1. Subsequently, as illustrated in FIG. 11A, the suction system 1 is caused to reach the distal side of the blood clots 300 along the guide wire 90 (Step S10). Note that a support catheter prepared separately may be used for causing the guide wire 90 to reach the distal side of the blood clots 300.

Subsequently, the suction catheter 30 is moved to the proximal side while restricting the movement of the pressing shaft 40 with the hand. At this time, the distal end portion of the pressing shaft 40 comes into contact with the proximal side coupling portion 60. Accordingly, movements of the expansion portion 20, the closing member 70, and the auxiliary expansion portion 80 are restricted and thus the positions of the expansion portion 20, the closing member 70, and the auxiliary expansion portion 80 in the blood vessel may be adjusted as desired. Then, the suction catheter 30 is moved to the proximal side with respect to the pressing shaft 40, and thus the auxiliary expansion portion 80, the expansion portion 20, and the closing member 70 are discharged in sequence from the sheath tubular member 31. Accordingly, as illustrated in FIG. 11B, the auxiliary expansion portion 80 is expanded by the restoration force of the expansion portion 80, digs (i.e., pushes or thrusts) into the blood vessel while expanding the blood vessel, and is firmly fixed to the blood vessel.

When the expansion portion 20 and the closing member 70 are discharged from the sheath tubular member 31, the distal side coupling portion 50 moves toward the proximal side coupling portion 60. The expansion portion 20 is then expanded to the optimal size by its own restoration force and comes into contact with the surface of the intravascular wall (Step S11). The expansion portion 20, being formed into a mesh-shape, digs into the surface of the intravascular wall and is firmly fixed. In accordance with an exemplary embodiment, the maximum expandable diameter of the expansion portion 20 to be used is larger than the diameter of the blood vessel to which the expansion portion 20 is inserted. Therefore, the expansion portion 20 cannot be expanded completely in the blood vessel and thus can be effectively fixed to the vascular wall by generating an expanding force.

Figure 12:
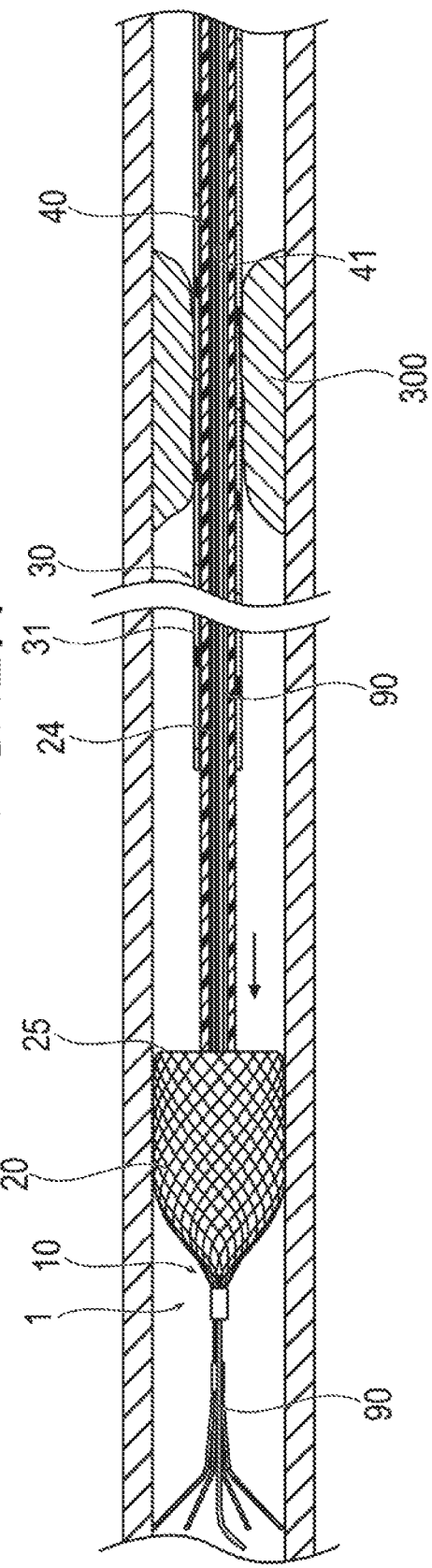
Figure 13:
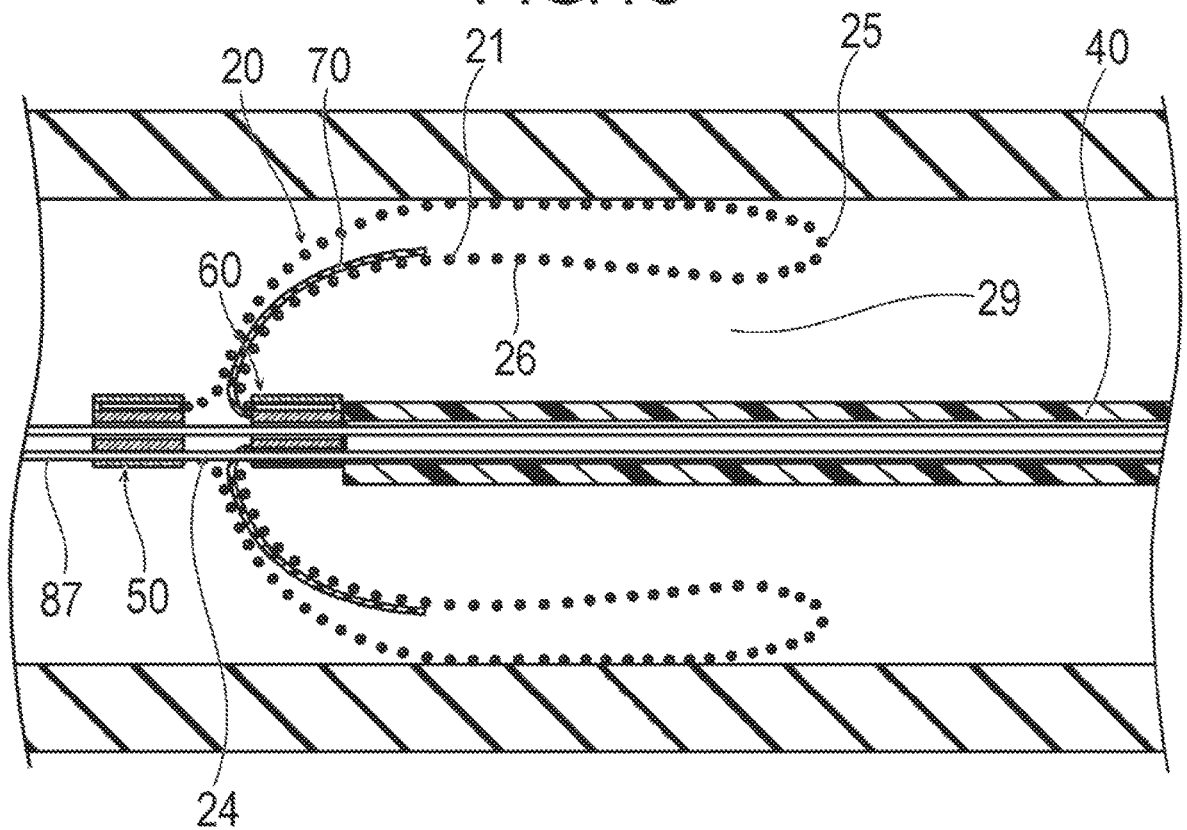
FIG. 13 is a cross-sectional view illustrating a state in which the expansion portion is indwelled in the blood vessel in a folded state.

Next, the pressing shaft 40 is moved toward the distal side, and the proximal side coupling portion 60 is pushed into the distal side by the distal end portion of the pressing shaft 40. Accordingly, as illustrated in FIG. 12A and FIG. 13, the expansion portion 20 assumes a folded state, which is a state of being folded back at the folded portion 25 (Step S12). The closing member 70 is located on the folded inner portion 26 on a center side with respect to the folded portion 25, that is, on the side closer to the proximal side coupling portion 60. Accordingly, in accordance with an exemplary embodiment, the closing member 70 does not completely block the blood vessel in the folded state. Accordingly, the blood flow is maintained, and thus a burden on the living body can be reduced. In the folded state, the maximum outer diameter of the auxiliary expansion portion 80 is larger than the maximum outer diameter of the folded portion 25. In addition, in the folded state, the maximum outer diameter of the auxiliary expansion portion 80 is larger than the maximum outer diameter of the folded inner portion 26. In accordance with an exemplary embodiment, in the folded state, the maximum outer diameter of the auxiliary expansion portion 80 is larger than the maximum outer diameter of the closing member 70.

When folding the expansion portion 20 backward (i.e., towards the hand side or proximal side), the expansion portion 20 receives a force in a distal direction. However, since the auxiliary expansion portion 80 is provided on the distal side of the expansion portion 20, the expansion portion 20 is supported by the auxiliary expansion portion 80 and thus is maintained at an adequate position.

Next, the pressing shaft 40 is removed out of the living body with the suction catheter 30 left in the living body. At this time, the internal space 29 of the expansion portion 20 depressed in the axial direction is wider in an inner part than an entrance part, the folded state of the expansion portion 20 may be stably maintained. In addition, since the shape of the closing member 70 at least partly folded is stabilized, the folded state of the expansion portion 20 may be stably maintained. In addition, since the closing member 70 receives a force directed toward the distal side from the blood flow, the folded state of the expansion portion 20 can be stably maintained.

Figure 14:
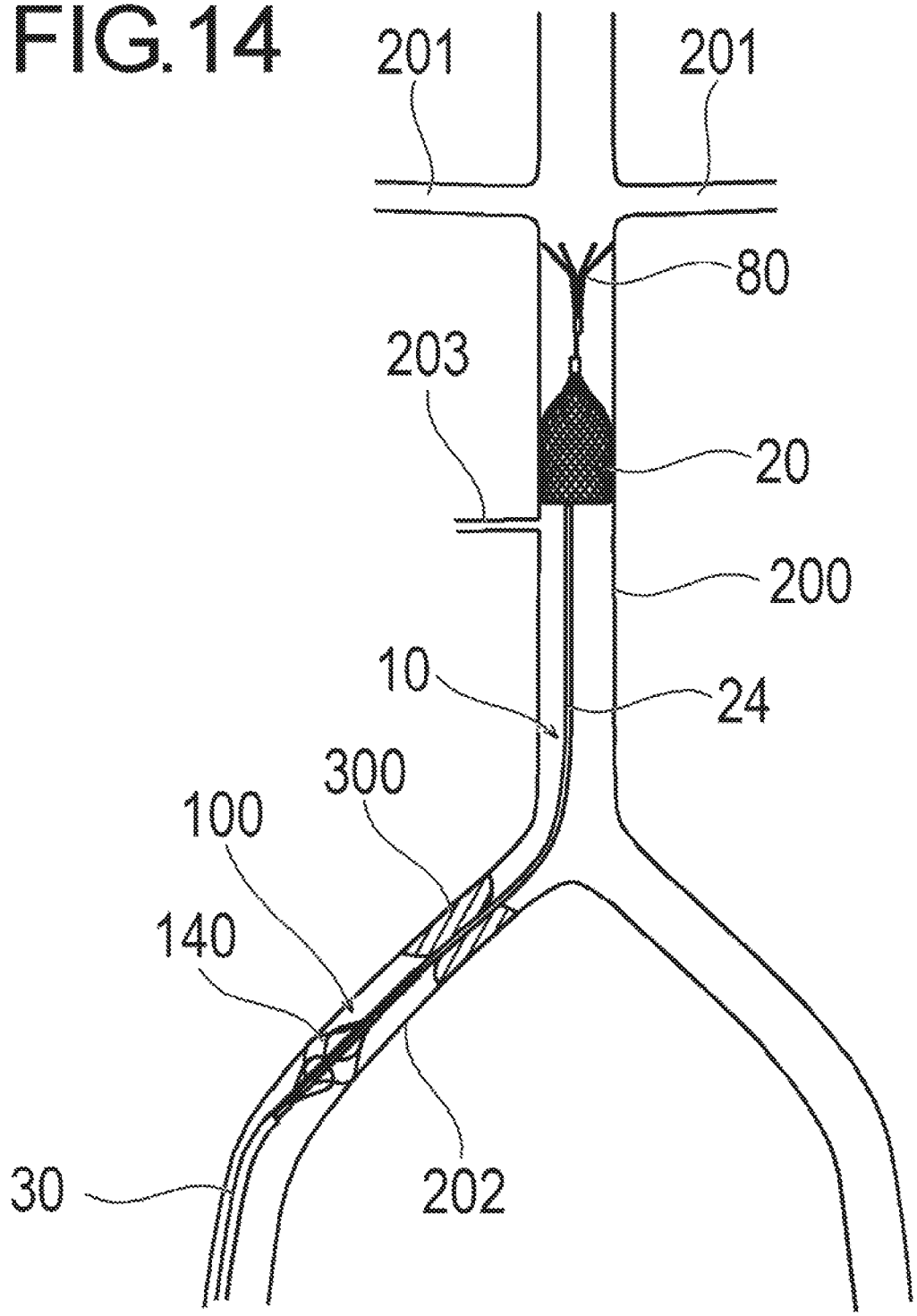
FIG. 14 is a schematic drawing illustrating an expanding tool in the blood vessel.

In accordance with an exemplary embodiment, the expansion portion 20 in the folded state and the auxiliary expansion portion 80 are preferably located on the proximal side (lower leg side) than a joint portion with a renal vein 201 of a vena cava 200 as illustrated in FIG. 14. The blood clots 300 can be located, for example, in an iliac vein 202. Accordingly, blood clots 301 (i.e., portions of blood clot 300) dropping (or breaking) off from the blood clots 300 can be prevented from flowing into the renal vein 201 and thus an increase in renal impression can be prevented or reduced to improve safety.

When the expansion portion 20 and the auxiliary expansion portion 80 are placed on the surface of the intravascular wall, the closing member 70 blocks part of the blood vessel. Accordingly, the blood flow in the blood vessel is reduced. Since the blood vessel is not completely blocked at this time, the blood flow is maintained, the burden on the living body may be reduced.

Next, the proximal end portion of the shaft portion 24 is inserted into the guide wire lumen of the breaking device 100. Next, the distal portion of the distal portion of the driving shaft 110 including the breaking member 140 is inserted into the Y connector 190 connected to the suction catheter 30 by being guided by the shaft portion 24. Subsequently, the driving shaft 110 is advanced and the breaking device 100 is inserted into the proximal side of the blood clots 300 as illustrated in FIG. 12B. After insertion, when the suction catheter 30 is moved to the proximal side, the breaking member 140 is expanded in the blood vessel as illustrated in FIG. 14 and FIG. 15A.

When rotating and moving the breaking member 140 in the axial direction for breaking blood clots, the syringe 180 containing the thrombolytic agent may be connected to the side tube 191 at a hand-side of the suction catheter 30. Then, a plunger of the syringe 180 is pushed at the same time of breaking of the blood clots 300 by the breaking member 140, so that the thrombolytic agent may be injected from the distal end portion of the suction catheter 30. Injection of the thrombolytic agent may be performed continuously or intermittently, and the speed and the amount of injection may be changed as needed. When the thrombolytic agent is injected intermittently, the thrombolytic agent may be suctioned (i.e., sucked) during stops of the injection. At this time, since the blood flow is lowered in the area where the blood clots are formed, the thrombolytic agent can be maintained at a relatively high concentration and thus higher effect of the thrombolytic agent can be expected. Note that the thrombolytic agent does not have to be used. When rotating and moving the breaking member 140 in the axial direction, the suction syringe 180 may be connected to the side tube 191 at the hand-side of the suction catheter 30. Then, the blood clots 301 broken by the suction catheter 30 may be suctioned (i.e., sucked) by pulling the plunger of the syringe 180 at the same time of breaking of the blood clots 300 by the breaking member 140. Note that the blood clots 301 do not have to be suctioned at the time of breaking.

Next, the driving shaft 110 is rotated by the rotary drive unit 150 with the breaking member 140 inserted to a position in the vicinity of the blood clots 300. Accordingly, the breaking member 140 rotates and the blood clots 300 adhering to the blood vessel are broken as illustrated in FIG. 15B (Step S13).

Figure 16:
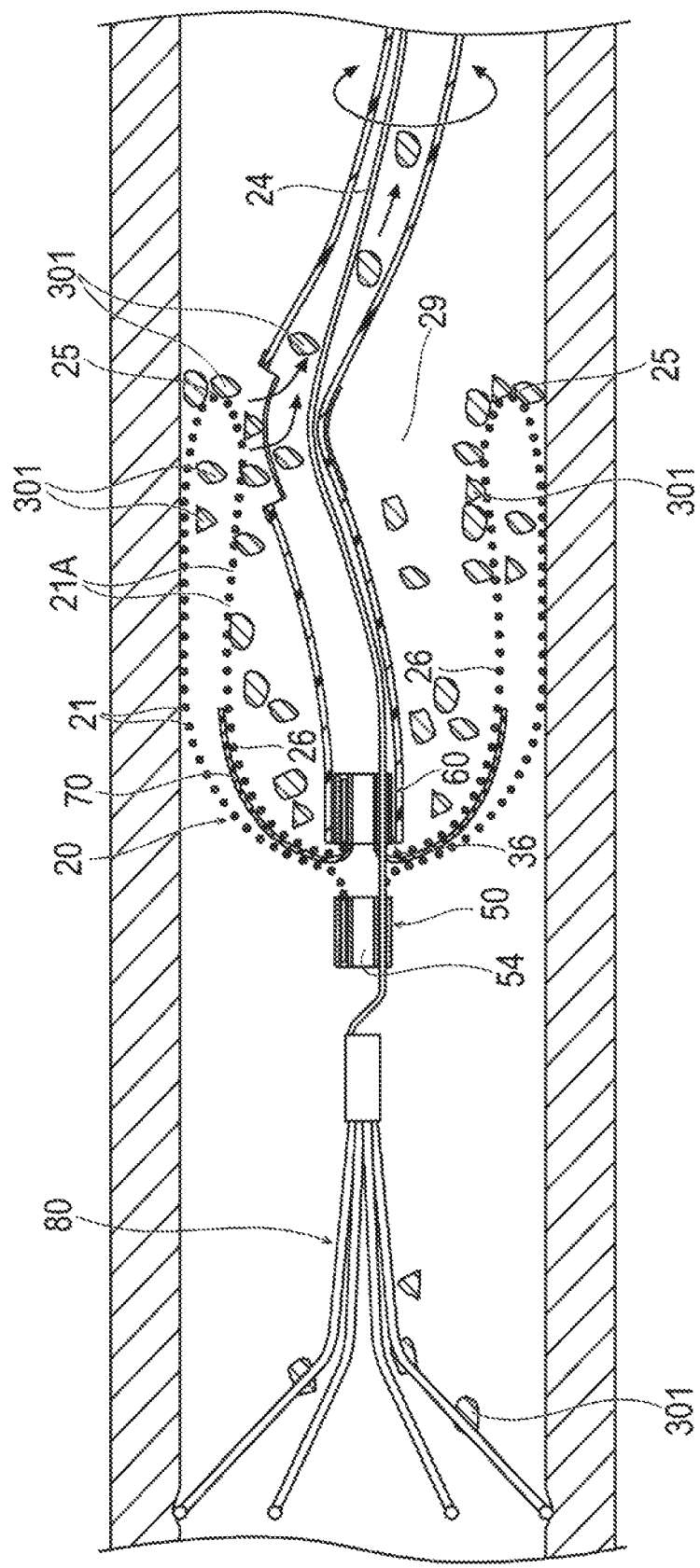
FIG. 16 is a cross-sectional view illustrating a state in which blood clots collected by the expansion portion and the closing member are suctioned by the suction catheter.

The blood clots 301 broken by the breaking member 140 reach the expansion portion 20 located on the downstream side as illustrated in FIG. 16. The gaps 21A of the expansion portion 20 in the folded state are partly closed by the closing member 70. Therefore, blood stays within a range blocked by the closing member 70. Therefore, broken blood clots 301 float in the blood vessel where the blood clots 301 stay. The blood can pass through the expansion portion 20 through the gaps 21A which are not blocked by the closing member 70. The expansion portion 20 is folded back at the folded portion 25 in a state in which the inner surfaces stay away from each other without contact. Therefore, the expansion portion 20 does not overlap in contact with each other at the folded portion 25 and thus the gaps 21A of the expansion portion 20 are desirably left (i.e., remain), such that the flow path can be maintained. Therefore, for example, the blood flowing through the gaps 21A of the expansion portion 20 can be appropriately maintained and thus the burden on the living body can be reduced. Since the inner surfaces of the expansion portion 20 do not overlap in contact with each other at the folded portion 25, a wide range of the expansion portion 20 may be allocated for a function as a filter. In accordance with an exemplary embodiment, if the inner surfaces of the expansion portion 20 overlap in contact with each other, the expansion portion 20 assumes a collapsed state, and thus the range that allows the blood to flow from the outer surface to the inner surface of the expansion portion 20 can be reduced. In contrast, the wide range of the expansion portion 20 may be allocated for the function as a filter, and thus clogging of the gaps 21A with the object can be prevented or reduced.

The blood clots 301 passed through the gaps 21A of the expansion portion 20 located outside the closing member 70 in the folded state enter from the outer surface side to the inner surface side of the expansion portion 20. The blood clots 301 are then trapped by the inner peripheral surface of the expansion portion 20 located on the distal side of the folded inner portion 26 in the folded state (Step S14). When the inner peripheral surfaces of the expansion portion 20 overlap in contact with each other at the folded portion 25, the expansion portion 20 assumes a collapsed state. Therefore, when passing through the gaps 21A, the blood clots 301 pass through the overlapped gaps 21A simultaneously. Therefore, when the inner peripheral surfaces of the expansion portion 20 overlap in contact with each other at the folded portion 25, the blood clots 301 passed through the gaps 21A of the expansion portion 20 from the outer peripheral surface side may not be retained in the inner peripheral surface side of the expansion portion 20. In contrast, since the expansion portion 20 is folded in a state in which the inner peripheral surfaces are separated from each other at the folded portion 25, the blood clots 301 passed through the gaps 21A in the folded portion 25 from the outer peripheral surface side together with the blood flow can be rather easily retained on the inner peripheral surface side of the expansion portion 20. Therefore, both of the outer surface side and the inner surface side of the expansion portion 20, which is doubled by being folded, may be effectively used for desirably trapping the blood clots 301.

The blood clots 301 passed through the expansion portion 20 doubled by being folded are further trapped by the auxiliary expansion portion 80 that functions as a filter.

Next, the rotational movement of the driving shaft 110 is stopped. Subsequently, the breaking member 140 is accommodated in the suction catheter 30 and the breaking device 100 is removed out from the blood vessel with the expanding tool 10 and the suction catheter 30 left (remaining) in the blood vessel. Note that the state in which the Y connector 190 is connected to the hub 32 of the suction catheter 30 can be maintained.

Next, the suction catheter 30 is moved to the distal side along the shaft portion 24. Accordingly, the suction catheter 30 is located on the proximal side of the expansion portion 20. Next, the Y connector 190 is connected to the suction syringe 180. Next, the proximal side coupling portion 60 is inserted into the distal side opening 36 (Step S15). Accordingly, the distal side opening 36 is closed.

Figure 17:
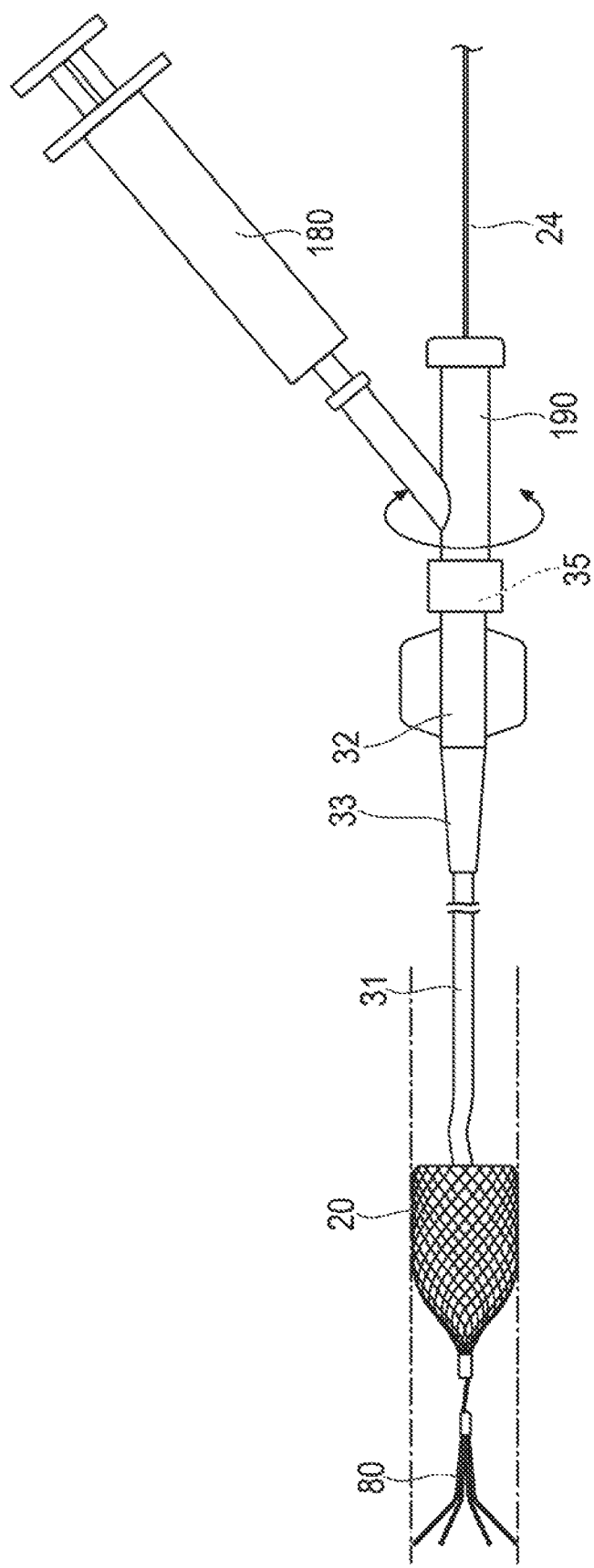
FIG. 17 is a plan view illustrating a state in which blood clots are suctioned by the suction catheter.

Next, as illustrated in FIG. 17, the plunger of the syringe 180 is pulled while holding and rotating the hub 32 and the Y connector 190. Accordingly, a negative pressure may be generated in the suction lumen 34. The distal side opening 36 is blocked by the proximal side coupling portion 60, and thus the suction force may be concentrated on the suction port 37. The suction port 37 is located on the distal side of the folded portion 25. In addition, the expansion portion 20 having the gaps 21A not closed by the closing member 70 is located in front (direction of opening) of the suction port 37. Therefore, the blood clots 301 trapped by the expansion portion 20 may be effectively suctioned (Step S16). Furthermore, the sheath tubular member 31 is bent at the bent portion 38 and thus the suction port 37 may be located closer to the expansion portion 20. Therefore, the blood clots 301 trapped by the expansion portion 20 may be effectively suctioned from the suction port 37. In addition, rotation of the sheath tubular member 31 causes a circular motion of the bent portion 38 and the blood around the bent portion 38 is stirred or rotated. Depending on the case, in accordance with an exemplary embodiment, the side surface of the sheath tubular member 31 comes into contact with the expansion portion 20 and the blood clots 301 trapped by the expansion portion 20. Accordingly, the blood clots 301 adhering to the expansion portion 20 are allowed to be separated from the expansion portion 20 by the blood flow, the contact of the sheath tubular member 31 with the blood clots 301, or an impact transferred from the sheath tubular member 31 to the expansion portion 20. The blood clots 301 separated from the expansion portion 20 are effectively suctioned from the suction port 37. Since the suction port 37 is located on a side where the bent portion 38 projects, the suction port 37 is located outside the rotation when the sheath tubular member 31 rotates. Therefore, the suction port 37 moves closer to the expansion portion 20 and the blood clots 301 adhering to the expansion portion 20, and depending on the case, comes into contact with the expansion portion 20 or the blood clots 301, so that the blood clots 301 adhering to the expansion portion 20 are effectively suctioned.

Since the closing member 70 is located on the distal side of the distal side opening 36, rotation of the sheath tubular member 31 causes the blood clots 301 remaining in the range where the blood flow is limited by the closing member 70 to rotate. Accordingly, the blood clots 301 move and are suctioned into the suction port 37. In the range where the flow is limited by the closing member 70, the blood clots 301 remain without adhering to the expansion portion 20 and thus may be suctioned from the suction port 37 even when the distal side opening 36 is closed. In accordance with an exemplary embodiment, the necessity of making a suction force act on this area can be relatively low. Therefore, the suction force can be concentrated to the suction port 37 by closing the distal side opening 36 by the proximal side coupling portion 60. Accordingly, the blood clots 301 trapped by the expansion portion 20 may be effectively suctioned from the suction port 37. Since the opening area of the suction port 37 is larger than the cross-sectional area of the suction lumen 34, suction over a wide range along the axial direction can be enabled. In addition, probability of clogging of the blood clots 301 suctioned into the suction port 37 can be reduced, and a relatively high suction force may be maintained.

In accordance with an exemplary embodiment, the proximal side coupling portion 60 inserted into the distal side opening 36 stabilizes the position of the expansion portion 20 and the suction catheter 30. Accordingly, a relatively stable procedure can be provided without depending on the technique of an operator.

In accordance with an exemplary embodiment, the sheath tubular member 31 is movable in the axial direction with respect to the proximal side coupling portion 60 within a range of an axial length L2 (see FIG. 3A) of the proximal side coupling portion 60. In accordance with an exemplary embodiment, the sheath tubular member 31 may be moved within a range in which the proximal side coupling portion 60 is not disconnected from the sheath tubular member 31. In this range, since the distal side opening 36 is closed by the proximal side coupling portion 60, and the suction force of the suction port 37 is not lowered. In addition, in this range, movement of the sheath tubular member 31 in the axial direction moves the suction port 37 and thus suction for the expansion portion 20 over a wide range in the axial direction can be enabled. The blood clots 301 suctioned by the suction port 37 are discharged to the syringe 180 through the suction lumen 34.

In this exemplary embodiment, since the closing member 70 limits part of the blood flow, the broken blood clots 301 float in the blood staying in the closing member 70. Therefore, the blood clots 301 may be efficiently suctioned from the suction port 37 and may be removed from the interior of the blood vessel. When the blood flows, a strong suction force may be required for suctioning the blood clots 301. However, in this exemplary embodiment, the closing member 70 limits the blood flow. Therefore, the suction force at the suction port 37 can be easily made to act for effective suctioning of the blood clots 301. Therefore, even the blood clots 301 adhering to a portion of the expansion portion 20 where the closing member 70 is not provided may be suctioned and removed rather effectively.

The closing member 70 is placed on the folded inner portion 26 side with respect to the folded portion 25. Therefore, the closing member 70 is placed at a position corresponding to the internal space 29 of the expansion portion 20 depressed in the axial direction in the folded state.

Therefore, the blood flow in the internal space 29 can be effectively reduced, and the blood clots 301 flowing into the internal space 29 may be desirably trapped. The closing member 70 is disposed at an end portion on the side (proximal side) where the folded inner portion 26 of the expansion portion 20 is located. Accordingly, the suction port 37 that performs suction can be rather easily guided to the area where the closing member 70 is disposed and the blood stays (especially in the internal space 29) by being guided by the shaft portion 24. Accordingly, a large amount of the floating blood clots 301 trapped in the internal space 29 may be efficiently suctioned through the suction port 37.

In addition, the closing member 70 does not completely block the blood vessel in the folded state, and thus the blood flow is maintained. Therefore, even when a side branch 203 is present in the vicinity of a position where the expansion portion 20 or the auxiliary expansion portion 80 is provided as illustrated in FIG. 14, the blood clots 301 are less likely to flow into the side branch 203, and safety can be improved.

When the blood clots 300 are broken and removed by being suctioned by the suction catheter 30, a force is applied to the expansion portion 20, the closing member 70, and the auxiliary expansion portion 80 from the blood flow or the suction catheter 30. However, the positions of the expansion portion 20, the closing member 70, and the auxiliary expansion portion 80 are adequately maintained by the auxiliary expansion portion 80. Therefore, the suction system 1 adequately achieves the procedure of trapping, suctioning and removing the blood clots 301.

After the suction of the blood clots 301 is completed, the suction catheter 30 is pushed toward the distal side by reciprocating (i.e., moving forward and backward) the suction catheter 30 as illustrated in FIG. 18. Accordingly, the wire members 21 are gradually accommodated in the interior of the suction lumen 34. Accordingly, the proximal side coupling portion 60 moves toward the proximal side in the interior of the suction lumen 34 and moves away from the distal side coupling portion 50. The expansion portion 20 and the closing member 70 are reduced in diameter while restoring from the folded state and is accommodated in the interior of the suction catheter 30 (Step S17). In addition, by pushing the suction catheter 30 to the distal side or by pulling the shaft portion 24 to the proximal side, the auxiliary expansion portion 80 is reduced in diameter and is accommodated in the suction catheter 30. At this time, the auxiliary expansion portion 80 is inclined toward the distal side and thus is accommodated smoothly in the interior of the suction catheter 30. When the expansion portion 20, the closing member 70, and the auxiliary expansion portion 80 are accommodated in the interior of the suction catheter 30, the blood clots 301 adhering thereto to the expansion portion 20, the closing member 70, and the auxiliary expansion portion 80 are also accommodated in the interior of the suction catheter 30, so that relatively high safety can be ensured.

After the expansion portion 20, the closing member 70, and the auxiliary expansion portion 80 are accommodated in the interior of the suction catheter 30, the expanding tool 10 is removed from the blood vessel together with the suction catheter 30 to complete the procedure (Step S18).

As described above, the suction system 1 according to the first exemplary embodiment is a system configured to trap and suction the blood clots 301 (objects) in a blood vessel (biological lumen) by being inserted into the blood vessel, including: the elongated shaft portion 24; the expansion portion 20 being a cylindrical member, the cylindrical member including a plurality of gaps 21A and being resiliently deformable; the proximal side coupling portion 60 provided at the proximal portion of the expansion portion 20 and having the outer diameter larger than the shaft portion 24, the shaft portion 24 being coupled to the proximal side coupling portion 60 fixedly in position or movably; and the suction catheter 30 movably accommodating the shaft portion 24 and being provided with the suction lumen 34 for making a suction force act from the proximal portion, in which the suction catheter 30 includes: the base member 31A having a tubular shape; and the distal side tubular portion 31B having a tubular shape and located on the distal side of the base member 31A, the distal side tubular portion 31B being inclined toward the predetermined direction X with respect to the central axis of the base member 31A, the distal side tubular portion 31B includes: the distal side opening 36 provided at a distal end of the distal side tubular portion 31B and configured to allow entry of the proximal side coupling portion 60; and the suction port 37 opening at the side surface on the proximal side of the distal side opening 36, the opening area of the suction port 37 is larger than the cross-sectional area of the suction lumen 34; the suction port 37 opens toward a direction opposite from the direction of inclination X with respect to the base member 31A of the distal side tubular portion 31B. The suction system 1 configured as described above is capable of partly closing the distal side opening 36 by introducing the suction catheter 30 along the shaft portion 24 to the expansion portion 20, and inserting the proximal side coupling portion 60 into the distal side opening 36. Therefore, the suction force applied to the suction lumen 34 may be concentrated to the suction port 37 by closing the suction lumen 34 at the distal side opening 36. Therefore, the blood clots 301 trapped by the expansion portion 20 may be effectively suctioned from the suction port 37. The suction system 1 is used by inserting the proximal side coupling portion 60 into the distal side opening 36, the positions of the expansion portion 20 and the suction catheter 30 are stabilized and thus a stable procedure which does not depend on the operators can be achieved. In addition, as being commonly used for accommodation of the shaft portion 24 and suction of the blood clots 301, the suction lumen 34 may have the largest possible inner diameter and thus may provide a relatively high suction force compared with the case where a plurality of the lumens are provided. In addition, by closing the suction lumen 34 used commonly for accommodation of the shaft portion 24 and suction of the blood clots 301 at the distal side opening 36, the suction force applied to the suction lumen 34 may be concentrated to the suction port 37.

In accordance with an exemplary embodiment, the opening area of the suction port 37 is larger than the cross-sectional area of the suction lumen 34. Accordingly, suction can be achieved over a relatively wide range along the axial direction of the suction catheter 30, and probability of clogging of suctioned objects in the suction port 37 can be reduced, so that a relatively high suction force can be maintained.

In addition, the length L2 of the proximal side coupling portion 60 in a direction along the shaft portion 24 is equal to or smaller than the length L1 from the distal side opening 36 to the suction port 37 of the suction catheter 30. Accordingly, the proximal side coupling portion 60 does not reach the suction port 37 even when being entered into the suction lumen 34 from the distal side opening 36, and does not close the suction port 37. In the range of the length L2 of the proximal side coupling portion 60, the suction catheter 30 may be moved toward and away from the expansion portion 20 while maintaining the state in which the proximal side coupling portion 60 is entered into the distal side opening 36. Therefore, the blood clots 301 may be effectively suctioned without lowering the suction force applied to the suction port 37 over a wide range along the axial direction.

In accordance with an exemplary embodiment, the suction catheter 30 includes the bent portion 38 at the distal portion. Accordingly, rotation of the suction catheter 30 causes a circular motion of the bent portion 38. Therefore, the blood may be rotated by the circular motion of the bent portion 38, and depending on the case, the side surface of the sheath tubular member 31 comes into contact with the expansion portion 20 and the blood clots 301 trapped by the expansion portion 20. Accordingly, the blood clots 301 adhering to the expansion portion 20 are allowed to be separated from the expansion portion 20 by the blood flow, the contact of the sheath tubular member 31 with the blood clots 301, or an impact transferred from the sheath tubular member 31 to the expansion portion 20. The blood clots 301 floating due to the closing member 70 may be moved by the rotation of the sheath tubular member 31 and suctioned from the suction port 37. Therefore, even when there is a flow, the blood clots 301 may be suctioned effectively from the suction port 37.

The suction port 37 is located on a projecting side of the bent portion 38. Accordingly, the suction port 37 is located outside the bent portion 38 when the bent portion 38 is rotated for making a rotational force to act. Therefore, the blood clots 301 adhering to the expansion portion 20 are effectively suctioned from the suction port 37.

The suction catheter 30 includes a reinforcing portion 39 configured to reinforce a portion where the suction port 37 is provided. Accordingly, the suction catheter 30 can be prevented or reduced from being bent or collapsed at a position where the suction port 37 is provided. Therefore, lowering of the operability can be prevented or reduced, and the suction force may be appropriately maintained.

In accordance with an exemplary embodiment, the suction system 1 includes the closing member 70 disposed partly in the expansion portion 20 so as to close the gaps 21A of the expansion portion 20 and being flexibly deformable. Accordingly, the suction system 1 is capable of effectively suctioning the blood clots 301 trapped by the expansion portion 20 having the gaps 21A and the blood clots 301 floating by being limited in movement by the closing member 70 from the suction port 37.

In a state in which the proximal side coupling portion 60 is inserted into the distal side opening 36, the closing member 70 is located on the distal side of a portion where the distal side opening 36 of the suction catheter 30 is provided. Accordingly, since the necessity of generating a relatively strong suction force act is relatively low, the suction force is not effected on the proximal side of the closing member 70 where the blood clots 301 are limited in flow in the blood vessel and float without adhering to the closing member 70. Instead, however, the suction force may be concentrated on the suction port 37. Since the flexibly deformable closing member 70 is located on the distal side of the distal side opening 36 of the suction catheter 30, the distal side opening 36 may be closed effectively by the closing member 70.

In addition, the expansion portion 20 is allowed to assume the folded state in which the expansion portion 20 is folded in the axial direction so that the proximal portion is located inside the expansion portion 20. In this folded state, when the proximal side coupling portion 60 enters the distal side opening 36, a portion of the expansion portion 20 other than the portion where the closing member 70 is provided is located on the opening direction of the suction port 37. Accordingly, the suction force may be made to act effectively on the blood clots 301 adhering on the expansion portion 20, and thus the blood clots 301 may be suctioned from the suction port 37 even the blood flows.

The present disclosure also provides a treatment method for collecting and suctioning the blood clots 301 (objects) in the blood vessel (biological lumen) using the aforementioned suction system 1. The treatment method includes: a Step S10 of inserting a sheath accommodating the expansion portion 20 into a blood vessel; a Step S11 of pushing the expansion portion 20 out of the sheath on a downstream side of a lesion area in the blood vessel, expanding the expansion portion 20 by its own resilient force, and indwelling the expansion portion 20 in the blood vessel; a Step S13 for causing an object generated in the lesion area in the blood vessel to drop off from the lesion area; a Step S15 of moving the suction catheter 30 to a distal side along the shaft portion 24 to insert a proximal side coupling portion 60 into the distal side opening 36; and a Step S16 of moving the suction catheter 30 in an axial direction or a direction of rotation with respect to the expansion portion 20 while maintaining the state in which the proximal side coupling portion 60 is inserted into the distal side opening 36 and suctioning the object trapped in the expansion portion 20 from the suction port 37. The suction system 1 configured as described above is capable of partly closing the distal side opening 36 by introducing the suction catheter 30 along the shaft portion 24 to the expansion portion 20, and inserting the proximal side coupling portion 60 into the distal side opening 36. Therefore, the suction force applied to the suction lumen 34 may be concentrated to the suction port 37, and the blood clots 301 trapped in the expansion portion 20 may be effectively suctioned. Since the treatment method is performed with the proximal side coupling portion 60 inserted into the distal side opening 36, positions of the expansion portion 20 and the suction catheter 30 are stabilized and a stable procedure which does not depend on an operators can be provided.

Figure 20:
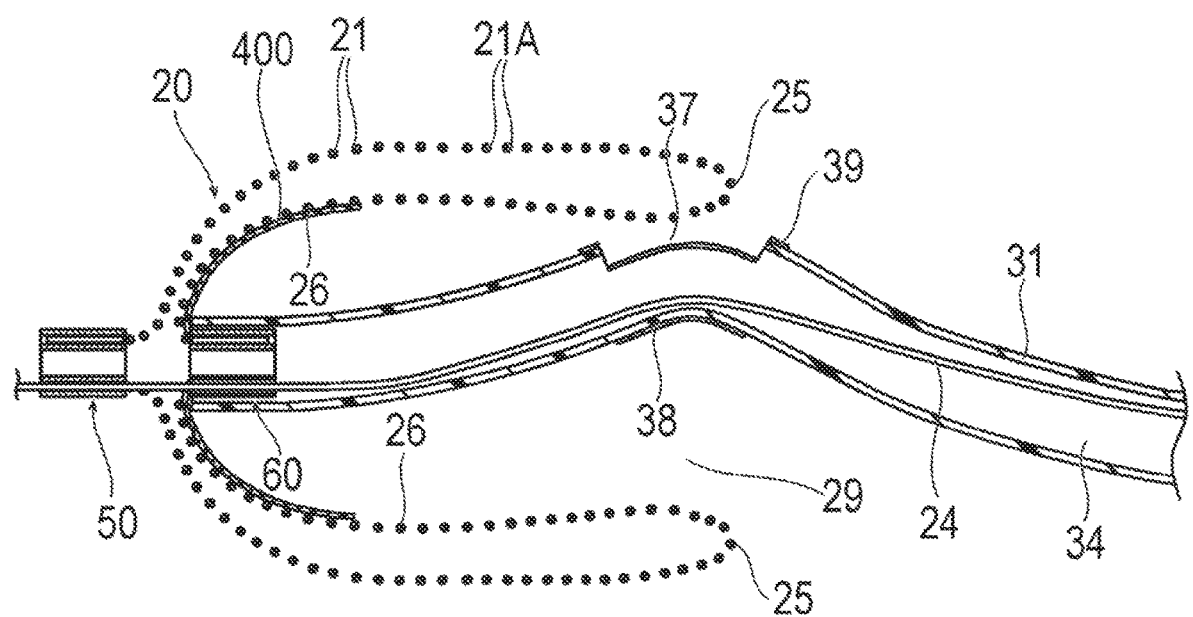
FIG. 20 is a cross-sectional view illustrating a modification of a suction system according to the first exemplary embodiment.

Note that a closing member 400 may be disposed on the proximal side (outer peripheral side) of the expansion portion 20 as in the modification of the first exemplary embodiment illustrated in FIG. 20. Accordingly, the closing member 400 is allowed to come into contact with the distal end portion of the sheath tubular member 31. Therefore, with the closing member 400 made of a flexible film-shape, the distal side opening 36 closed by the proximal side coupling portion 60 may be closed relatively reliably to further enhance the suction force of the suction port 37.

Figure 21:
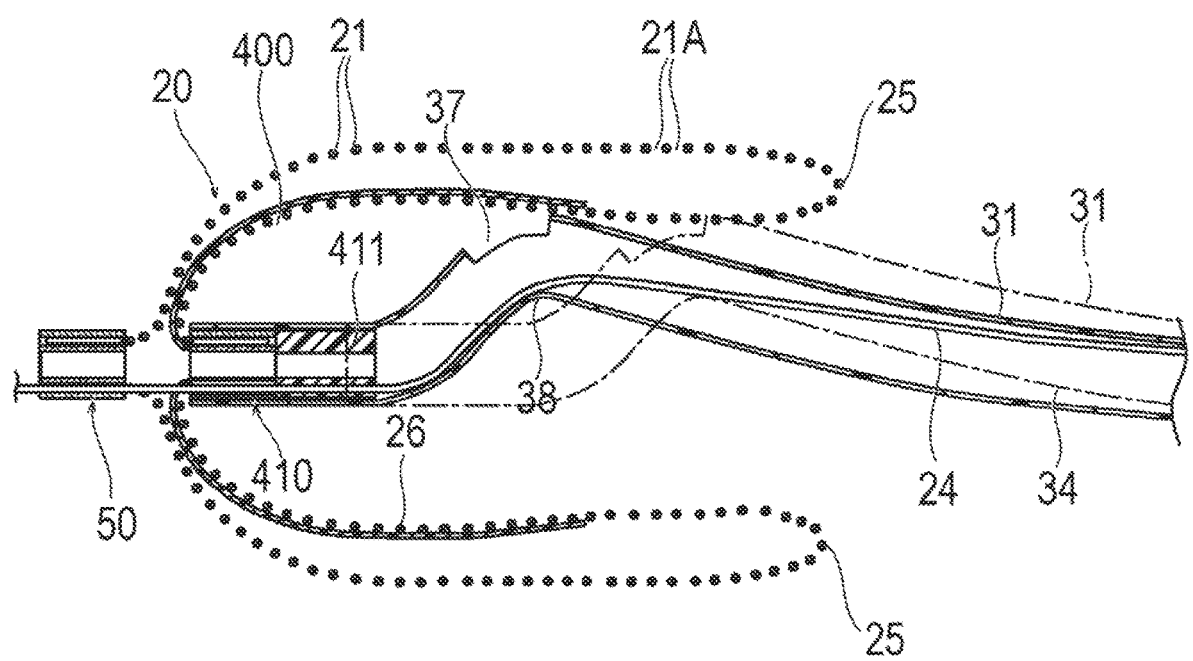
FIG. 21 is a cross-sectional view illustrating another modification of the suction system according to the first exemplary embodiment.

As in other modifications of the first exemplary embodiment illustrated in FIG. 21, a proximal side coupling portion 410 may have another extension member 411 fixed at a portion where the wire members 21 are fixed. Accordingly, the proximal side coupling portion 410 may be elongated in the axial direction. Therefore, the sheath tubular member 31 may be moved in the axial direction within a long range of the proximal side coupling portion 410 without reducing the suction force of the suction port 37. By moving the sheath tubular member 31, the suction port 37 may be allowed to move to a range surrounded by the closing member 70 and a range surrounded by the expansion portion 20 where the closing member 70 is not provided. Accordingly, both of the blood clots 301 floating in a state of being surrounded by the closing member 70 and the blood clots 301 adhering to the expansion portion 20 are effectively suctioned.

Second Embodiment

Figure 22:
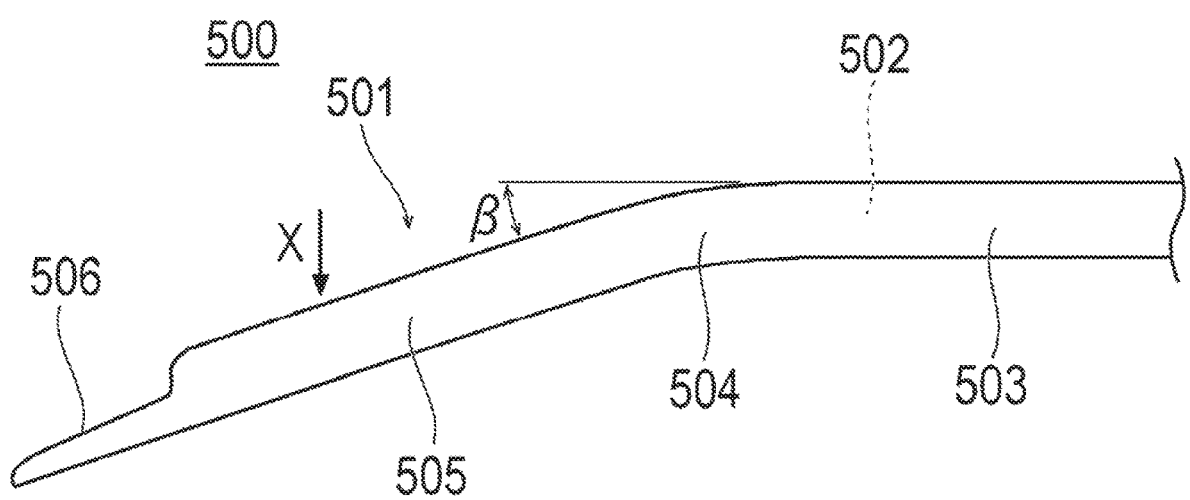
FIG. 22 is a plan view illustrating a suction catheter of a suction system according to a second exemplary embodiment.
Figure 23:
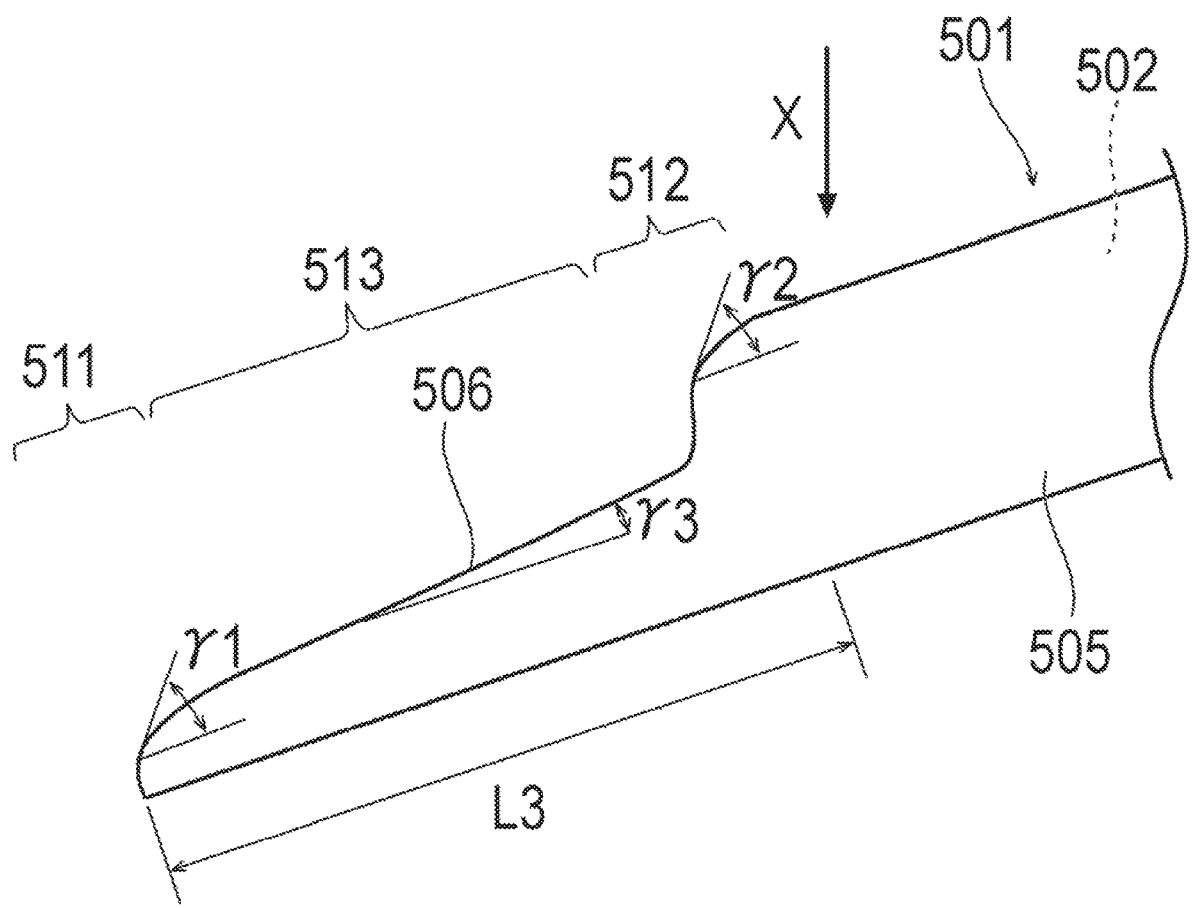
FIG. 23 is a plan view illustrating a distal portion of the suction catheter according to the second exemplary embodiment in an enlarged scale.
Figure 24:
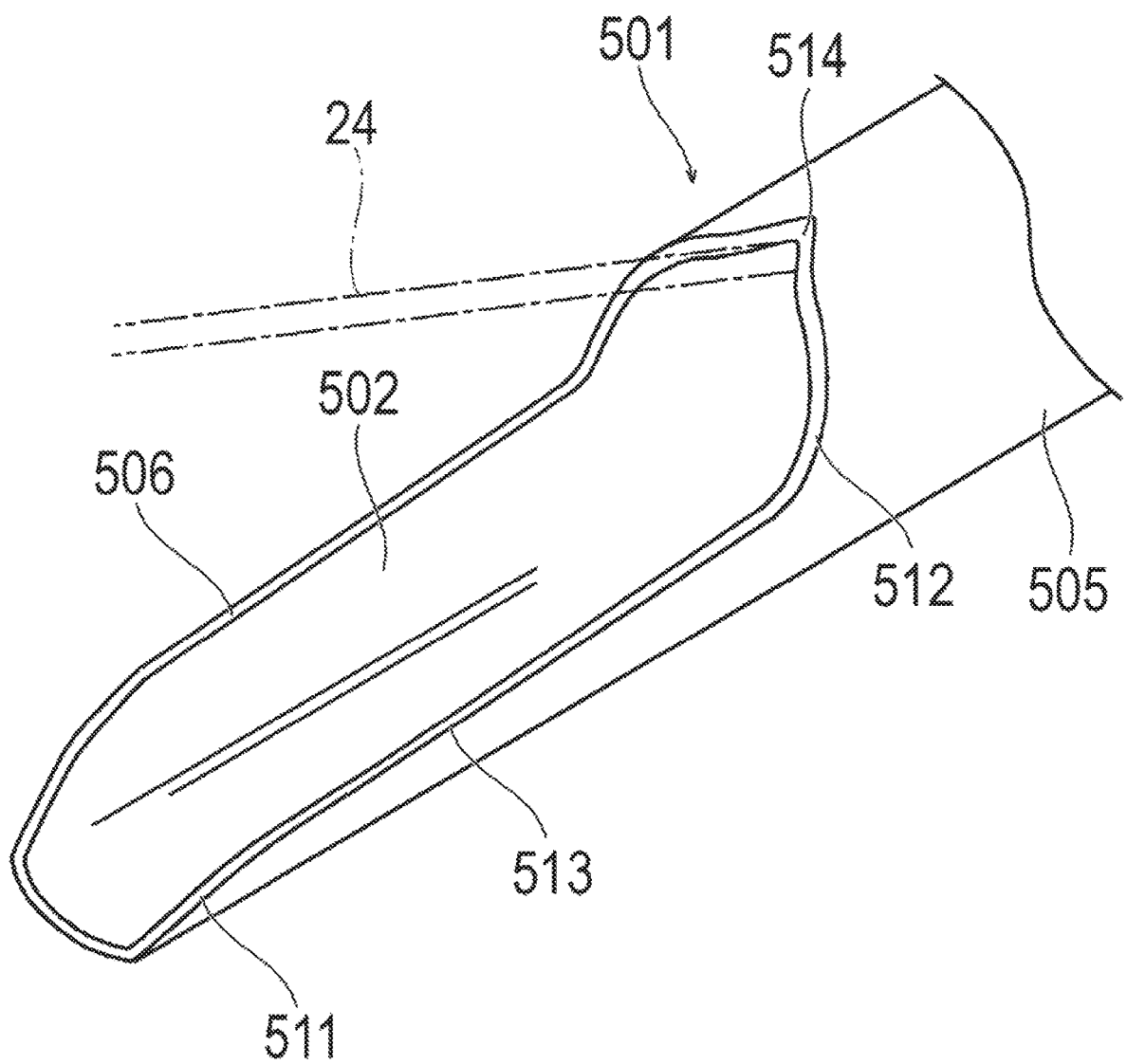
FIG. 24 is a perspective view illustrating the distal portion of the suction catheter according to the second exemplary embodiment in an enlarged scale.

A suction system according to a second exemplary embodiment of the present disclosure is different from the first exemplary embodiment only in configuration of a sheath tubular member 501 that constitutes a suction catheter 500 as illustrated in FIGS. 22 to 24. Note that portions having the same functions as those of the first exemplary embodiment are denoted by the same reference numerals and description is omitted.

The sheath tubular member 501 is capable of accommodating the expanding tool 10 (see FIG. 1) and is provided with a suction lumen 502 capable of making a suction force act from a proximal side. The sheath tubular member 501 includes a linear base member 503 located on the proximal side, a bent portion 504 located on a distal side of the base member 503, and a distal side tubular portion 505 located on the distal side of the bent portion 504. The bent portion 504 is curved or bent. Therefore, the distal side tubular portion 505 is inclined in a predetermined direction X with respect to the central axis of the base member 503. In accordance with an exemplary embodiment, an angle β of inclination of the distal side tubular portion 505 with respect to the base member 503 is not particularly limited. For example, the angle α ranges from 10 degrees to 90 degrees, more preferably from 30 degrees to 80 degrees, and more preferably, from 50 degrees to 70 degrees. The distal side tubular portion 505 includes a distal side opening 506 from which the suction lumen 502 opens at a distal end. The distal side opening 506 is inclined with respect to the central axis of the distal side tubular portion 505. The distal side opening 506 is opening toward a direction opposite from the direction X in which the distal side tubular portion 505 inclines with respect to the base member 503. A length L3 of the distal side opening 506 along the axial direction of the distal side tubular portion 505 is preferably longer than a length L4 of the proximal side coupling portion 60 in the axial direction (see FIG. 26).

In accordance with an exemplary embodiment, the distal side opening 506 includes a first portion 511 on the distal-most side, a second portion 512 on the proximal-most side, and a third portion 513 located between the first portion 511 and the second portion 512. In accordance with an exemplary embodiment, an angle of inclination γ1 of the first portion 511 with respect to the central axis of the distal side tubular portion 505 is larger than an angle of inclination γ3 of the third portion 513 with respect to the central axis of the distal side tubular portion 505. The angle of inclination γ1 increases toward the distal side. When the angle of inclination γ1 is reduced toward the distal side, a distal end of the first portion 511 becomes thin and pointed. In contrast, when the angle of inclination γ1 increases toward the distal side, the distal end of the first portion 511 does not become too thin.

Figure 25:
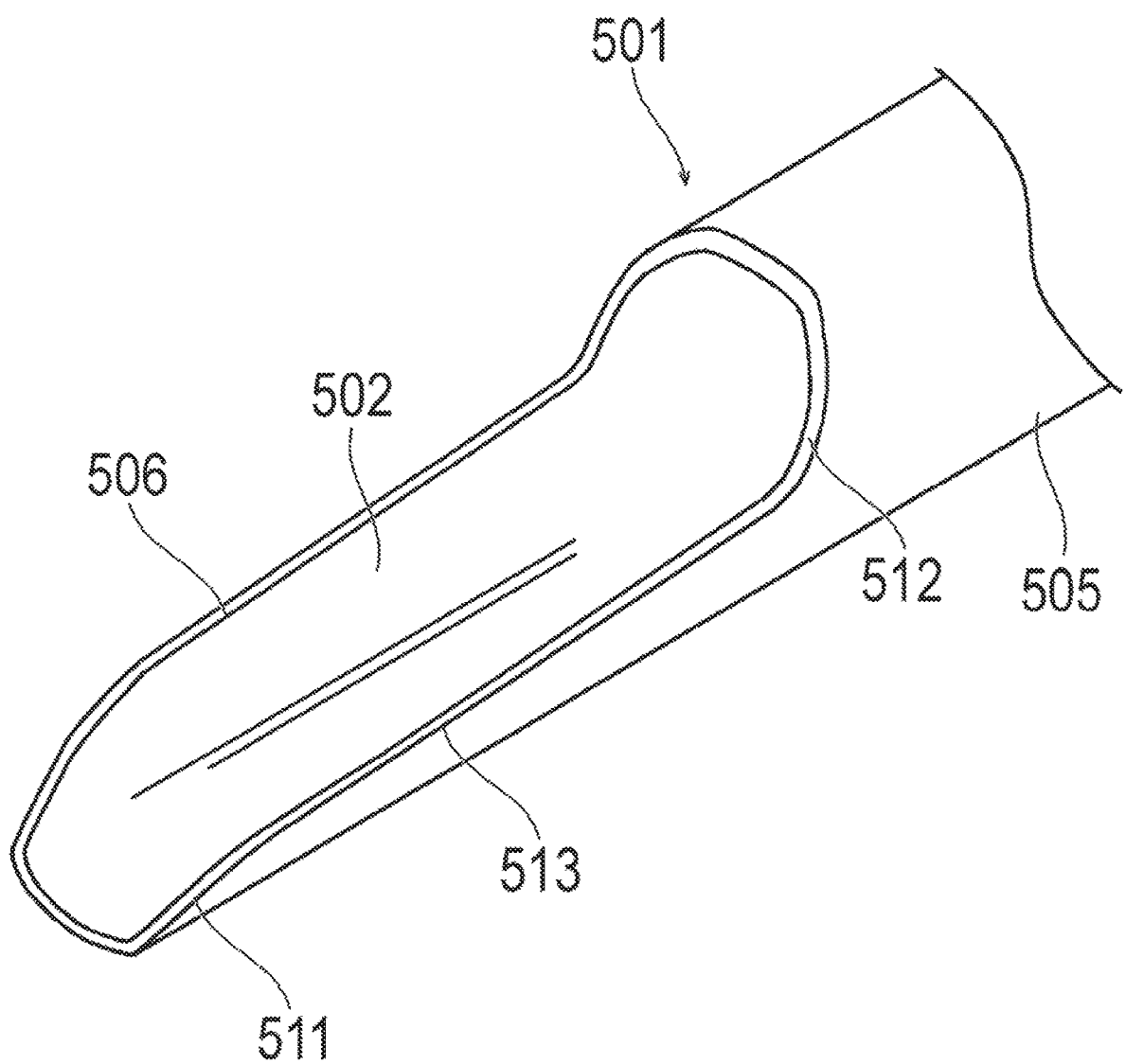
FIG. 25 is a perspective view illustrating a modification of a suction catheter according to the second exemplary embodiment.

In accordance with an exemplary embodiment, an angle of inclination γ2 of the second portion 512 with respect to the central axis of the distal side tubular portion 505 becomes larger than the angle of inclination γ3 once toward the proximal side from the third portion 513, and then is reduced. When the angle of inclination γ2 is reduced toward the distal side, an edge portion 514 at an end portion on the proximal side of the second portion 512 becomes thinner toward the proximal side. Note that the edge becoming thinner toward the proximal side does not have to be provided at an end portion of the proximal side of the second portion 512 as in a modification illustrated in FIG. 25.

Next, a method of using the suction system according to the second exemplary embodiment will be described.

Figure 26:
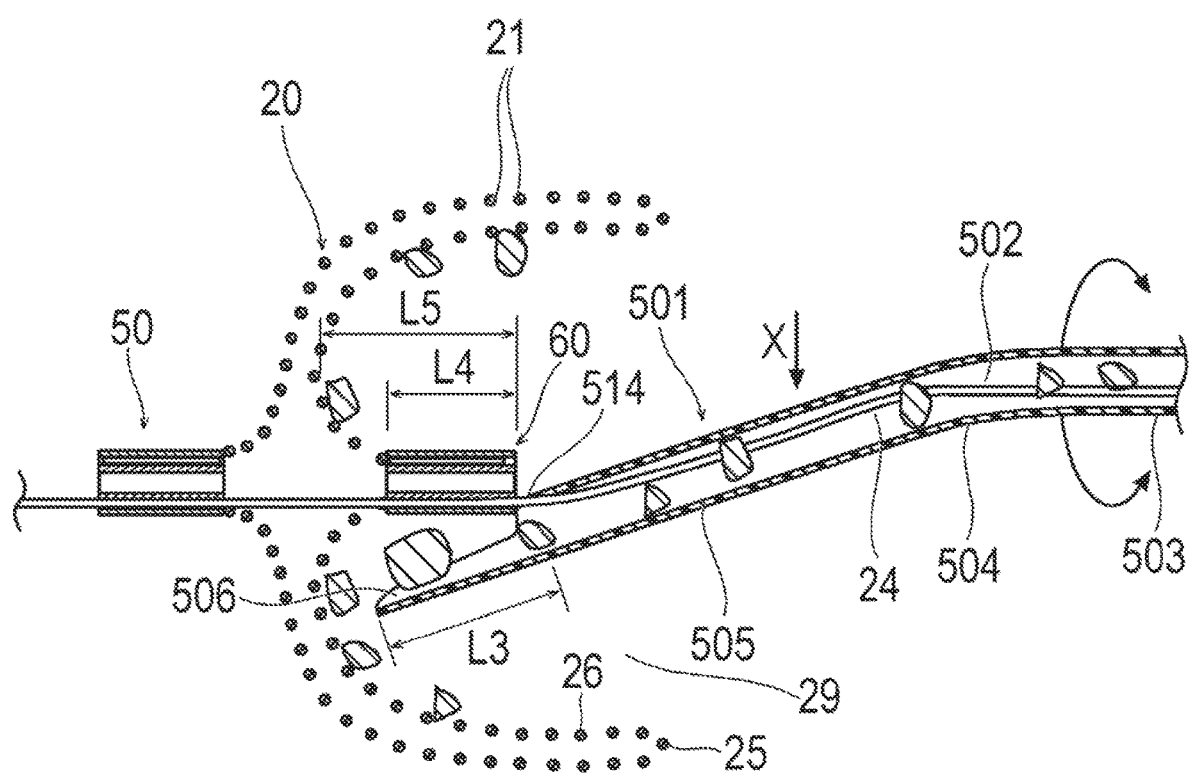
FIG. 26 is a cross-sectional view illustrating a state in which blood clots collected by an expansion portion are suctioned by the suction catheter.

First, in the same manner as the first exemplary embodiment, the expansion portion 20 is placed in the biological lumen by using the sheath tubular member 501 of the suction catheter 500. Next, the blood clots 300 are broken by the breaking device 100. Note that the expansion portion 20 will be described as not having the closing member 70. Next, the breaking device 100 is removed from the suction catheter 500. Subsequently, the suction catheter 500 is moved to the distal side along the shaft portion 24. Accordingly, as illustrated in FIG. 26, the distal side opening 506 is attached to the proximal side coupling portion 60 located at the proximal side of the expansion portion 20 in the expanded state. The second portion 512 or the edge portion 514 (see FIG. 24) is attached to the proximal side coupling portion 60 located on the proximal side of the expansion portion 20 in the expanded state. Next, the plunger of the syringe 180 is pulled. Accordingly, a negative pressure may be generated in the suction lumen 502. Accordingly, the blood clots 301 may be suctioned from the distal side opening 506. At this time, since the proximal side coupling portion 60 is attached to the distal side opening 506, positions of the expansion portion 20 and the suction catheter 500 are stabilized, and a stable procedure that does not depend on an operators can be achieved. At this time, the plunger of the syringe 180 may be pulled while holding the hub 32 and the Y connector 190 and rotating the suction catheter 500. Accordingly, a wide range of the expansion portion 20 may be suctioned.

The sheath tubular member 501 is bent at the bent portion 504. In addition, the distal side opening 506 is opening toward the direction opposite from the direction X in which the distal side tubular portion 505 inclines with respect to the base member 503. Therefore, the shaft portion 24 can be rather easily guided to the second portion 512 located on the proximal side of the distal side opening 506 as illustrated in FIGS. 24 and 26. The edge portion 514 of the second portion 512 on the proximal side becomes thinner. Therefore, when the suction catheter 500 is moved by being guided by the longitudinal shaft portion 24, the shaft portion 24 enters the edge portion 514, having a thin shape, of the distal side opening 506. Accordingly, a wide range of the distal side opening 506 on the distal side is left without being impaired by the shaft portion 24. Furthermore, since the distal side opening 506 is opened toward the direction opposite from the direction X in which the distal side tubular portion 505 is inclined, when the shaft portion 24 enters the edge portion 514 having a thin shape, the distal side opening 506 is easily faced toward the distal side. In addition, the shaft portion 24 is disposed radially outward of the proximal side coupling portion 60. Therefore, the distal side opening 506 is easily located on the side opposite from the proximal side coupling portion 60 with the shaft portion 24 interposed between the distal side opening 506 and the proximal side coupling portion 60. Therefore, the blood clots 301 trapped by the expansion portion 20 may be effectively suctioned from the distal side opening 506. The distal side opening 506 is inclined with respect to the central axis of the distal side tubular portion 505, and thus the opening area is larger than the cross-sectional area of the suction lumen 502. Therefore, suction over a relatively wide range can be achieved. In addition, probability of clogging of the blood clots 301 suctioned into the distal side opening 506 can be reduced, and a relatively high suction force may be maintained. Note that when the blood clots 301 larger than the cross-sectional area of the suction lumen 502 is suctioned from the distal side opening 506, the blood clots 301 are broken due to a negative pressure in the suction lumen 502, and are carried in the suction lumen 502.

In addition, the length L3 of the distal side opening 506 along the axial direction is longer than the length L4 of the proximal side coupling portion 60 along the axial direction.

Accordingly, suction by the distal side opening 506 is less likely to be affected by the proximal side coupling portion 60. Therefore, the blood clots 301 may be effectively suctioned from the distal side opening 506. In accordance with an exemplary embodiment, the length L3 of the distal side opening 506 is equal to or smaller than a length L5 from the proximal portion of the proximal side coupling portion 60 to the expansion portion 20 located on the distalmost side of the internal space 29. Accordingly, the distal end of the distal side tubular portion 505 is relatively less likely to enter the gaps 21A of the expansion portion 20. Accordingly, safety may be improved by preventing or reducing interference between the suction catheter 500 and the expansion portion 20.

In contrast, when the angle of inclination γ1 of the first portion 511 of the distal side opening 506 increases toward the distal side, the distal end of the first portion 511 does not become too thin. Therefore, the distal end of the distal side tubular portion 505 is less likely to enter the gaps 21A of the expansion portion 20. Accordingly, safety may be improved by preventing or reducing interference between the suction catheter 500 and the expansion portion 20.

The expansion portion 20 is capable of assuming the folded state in which the expansion portion 20 is folded in the axial direction so that the proximal portion is located inside the expansion portion 20. Therefore, after the blood clots 301 is effectively trapped by the expansion portion 20 which is folded, the blood clots 301 may be effectively suctioned by the suction catheter 500.

With the expansion portion 20 in the folded state, the entire part or part of the distal side opening 506 in a case where the distal side opening 506 is attached to the proximal side coupling portion 60 is located on the distal side of the folded portion 25. Accordingly, the expansion portion 20 that functions as a filter is located in front (distally) of the distal side opening 506. Therefore, blood clots adhering to the expansion portion 20 may be suctioned rather efficiently from the distal side opening 506. Note that the distal side opening 506 may be located on the proximal side of the folded portion 25 in the folded state.

After the suction of the blood clots 301 is completed, the expanding tool 10 is accommodated in the suction catheter 500 and is removed out from the blood vessel to complete the procedure.

Third Embodiment

Figure 27:
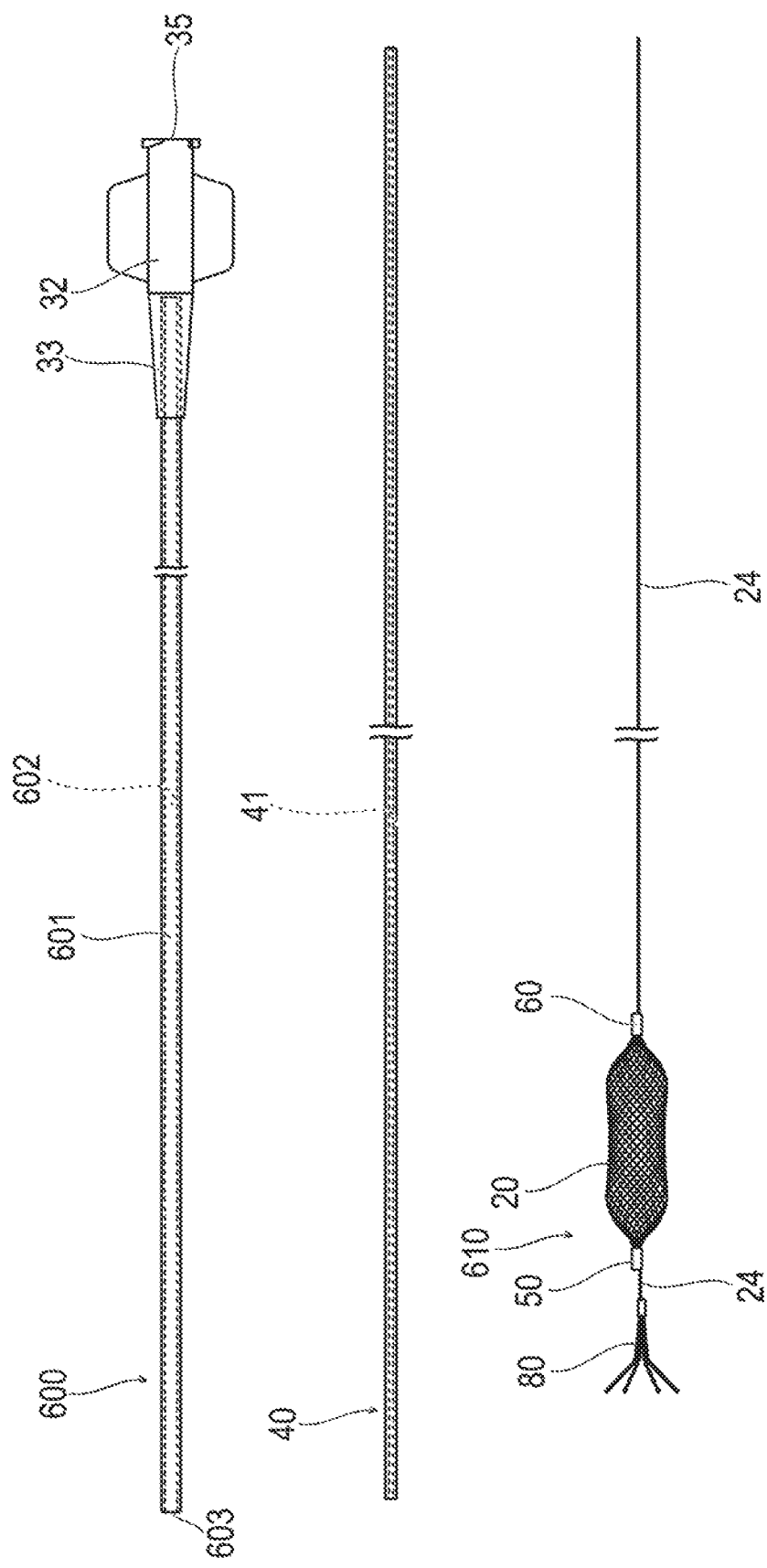
FIG. 27 is plan views illustrating a suction system according to a third exemplary embodiment.

A suction system according to a third exemplary embodiment of the present disclosure is different from the first exemplary embodiment only in configurations of a sheath tubular member 601 and an expanding tool 610 that constitute a suction catheter 600 as illustrated in FIG. 27. Note that portions having the same functions as those of the first exemplary embodiment are denoted by the same reference numerals and description is omitted.

The sheath tubular member 601 is capable of accommodating the expanding tool 610, and is provided with a suction lumen 602 capable of making a suction force act from a proximal side. In accordance with an exemplary embodiment, the sheath tubular member 601 is a linear tubular member and does not have an opening on a side surface of the sheath tubular member 601. The sheath tubular member 601 has a linear shape, but may be provided with a bent portion on a distal side. The sheath tubular member 601 includes a distal side opening 603 from which the suction lumen 602 opens at a distal end. The distal side opening 603 has an inner diameter sufficient for allowing entry of the proximal side coupling portion 60 of the expanding tool 10. The sheath tubular member 601 does not have the opening on the side surface, the suction force can be concentrated on the distal side opening 603.

Figure 28:
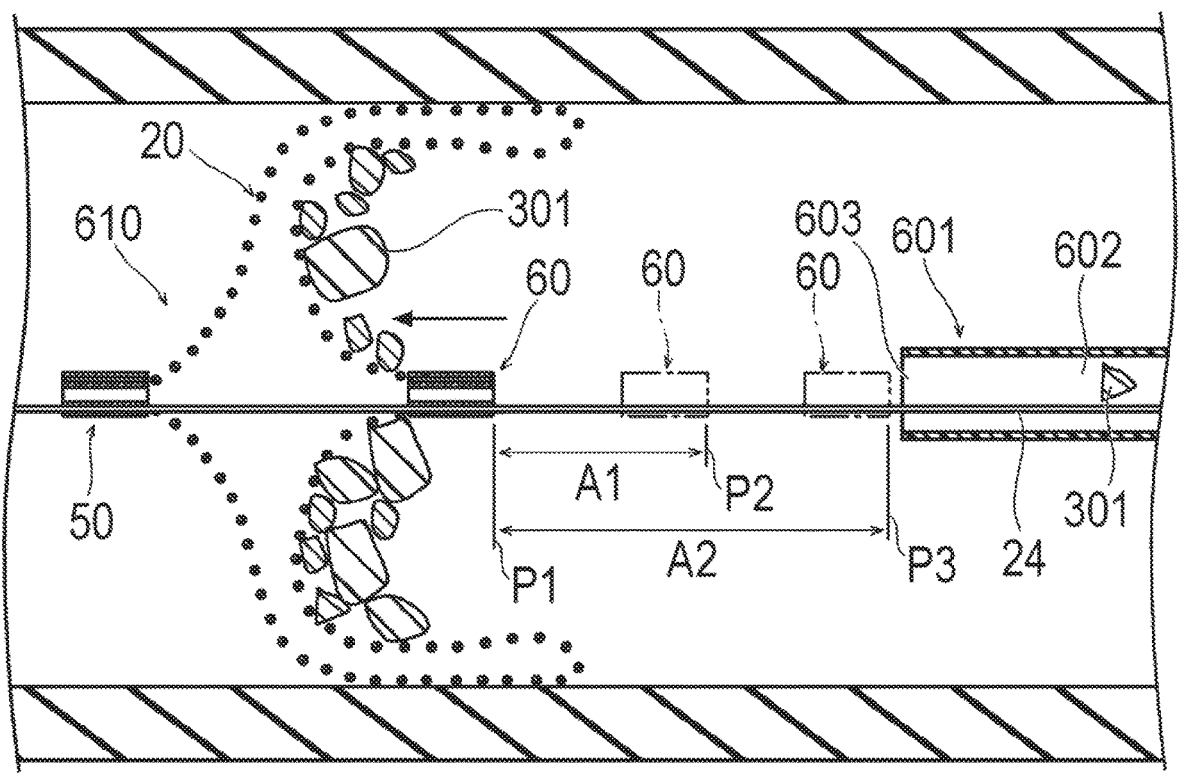
FIG. 28 is a cross-sectional view illustrating a state in which blood clots are suctioned by the suction catheter.

In accordance with an exemplary embodiment, the expansion portion 20 of the expanding tool 610 is not provided with a closing member 70 as illustrated in FIG. 28. Note that the expanding tool 610 is the same as the expanding tool 10 of the first exemplary embodiment except that the closing member 70 is not provided. The outer diameter of the proximal side coupling portion 60 is larger than the outer diameter of the shaft portion 24. The central axis of the proximal side coupling portion 60 is away from the central axis of a portion of the shaft portion 24 coupled to the proximal side coupling portion 60. In accordance with an exemplary embodiment, the proximal side coupling portion 60 and the shaft portion 24 are not coaxial.

Next, a method (treatment method) of using the suction system according to the third exemplary embodiment will be described.

First, in the same manner as the method of using described in the first exemplary embodiment, the expansion portion 20 is placed in the biological lumen by using the sheath tubular member 601 of the suction catheter 600. Next, the blood clots 300 are broken by the breaking device 100. The broken blood clots 301 are trapped by the expansion portion 20. Next, the breaking device 100 is removed from the suction catheter 600. Subsequently, the suction catheter 600 is moved to the distal side along the shaft portion 24. Accordingly, the distal side opening 603 is located on the proximal side of the proximal side coupling portion 60.

Next, the plunger of the syringe 180 is pulled. Accordingly, a negative pressure is generated in the suction lumen 602. Accordingly, the blood clots 301 are suctioned from the distal side opening 603 into the suction lumen 602. In an environment where the blood flows, the blood clots 301 do not float but adhere to the expansion portion 20. Therefore, the suction force of the distal side opening 603 may be insufficient for separating and removing the blood clots 301 from the expansion portion 20. Therefore, at least part of the blood clots 301 continues to a state of adhering to the expansion portion 20.

Figure 29:
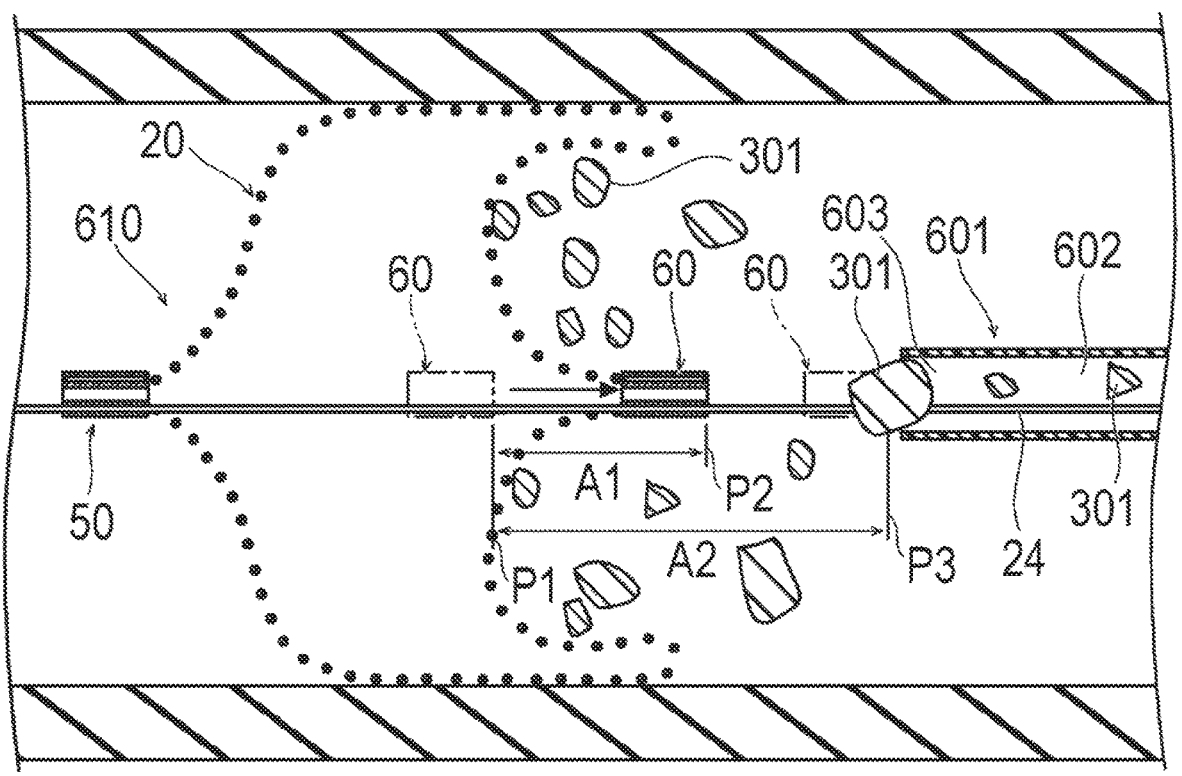
FIG. 29 is a cross-sectional view illustrating a state in which the shaft portion is moved toward a proximal side.

Next, with the position of the distal side opening 603 fixed, the shaft portion 24 is pulled to move the proximal side coupling portion 60 to the proximal side as illustrated in FIG. 29. The proximal side coupling portion 60 is, for example, moved from a position P1 to a position P2. Note that the proximal side coupling portion 60 does not enter the distal side opening 603. Subsequently, in a state in which the position of the distal side opening 603 is fixed, the shaft portion 24 is pushed to move the proximal side coupling portion 60 to the distal side. The proximal side coupling portion 60 is, for example, moved from the position P2 to the position P1. In this manner, by the reciprocal movement of the proximal side coupling portion 60 in an axial direction, at least part of the blood clots 301 adhering to the expansion portion 20 is separated and floats from the expansion portion 20 toward the proximal side. Therefore, the blood clots 301 separated from the expansion portion 20 can be suctioned from the distal side opening 603 into the suction lumen 602. When the proximal side coupling portion 60 repeats the reciprocal movement between the position P1 and the position P2, the blood clots 301 are separated in sequence from the expansion portion 20 and are suctioned in sequence from the distal side opening 603.

After the reciprocal movement of the proximal side coupling portion 60 is repeated between the position P1 and the position P2, the blood clots 301 may remain in the expansion portion 20. In such a case, with the position of the distal side opening 603 fixed, the proximal side coupling portion 60 is reciprocally moved in the axial direction in an amplitude A2 longer than an amplitude A1 between the position P1 and the position P2. The proximal side coupling portion 60 reciprocates, for example, between the position P1 and a position P3. With an increase in the amplitude A2 of the reciprocal movement of the proximal side coupling portion 60, the blood clots 301 adhering to the expansion portion 20 move significantly from the expansion portion 20 and are likely to be separated from expansion portion 20. When the proximal side coupling portion 60 repeats the reciprocal movement between the position P1 and the position P3, the blood clots 301 are separated in sequence from the expansion portion 20 and are suctioned in sequence from the distal side opening 603. Accordingly, the suction catheter 600 can suction the blood clots 301 rather effectively. Note that the proximal side coupling portion 60 may repeat the reciprocal movement only at a constant amplitude (for example, the amplitude A1 or the amplitude A2) without changing the amplitude. Alternatively, the amplitude of the reciprocal movement of the proximal side coupling portion 60 may vary among a number of amplitudes instead of being varied between the two amplitudes L1 and L2. In addition, the amplitude of the reciprocal movement of the proximal side coupling portion 60 may be increased and reduced repeatedly.

After the suction of the blood clots 301 is completed, the expanding tool 610 is accommodated in the suction catheter 600 and can be removed from the blood vessel to complete the procedure. Note that although the proximal side coupling portion 60 is moved with the position of the distal side opening 603 fixed in the method of using according to the third exemplary embodiment, the distal side opening 603 may be moved in the axial direction.

Next, another method (treatment method) of using the suction system according to the third exemplary embodiment will be described.

First, in the same manner as the method described in the first exemplary embodiment, the expansion portion 20 is placed in the biological lumen by using the sheath tubular member 601 of the suction catheter 600. Next, the blood clots 300 are broken by the breaking device 100. The broken blood clots 301 are trapped by the expansion portion 20. Next, the breaking device 100 is removed from the suction catheter 600. Subsequently, the suction catheter 600 is moved to the distal side along the shaft portion 24. The distal side opening 603 is located in the vicinity of the proximal side coupling portion 60 and on the proximal side of the proximal side coupling portion 60.

Figure 30:
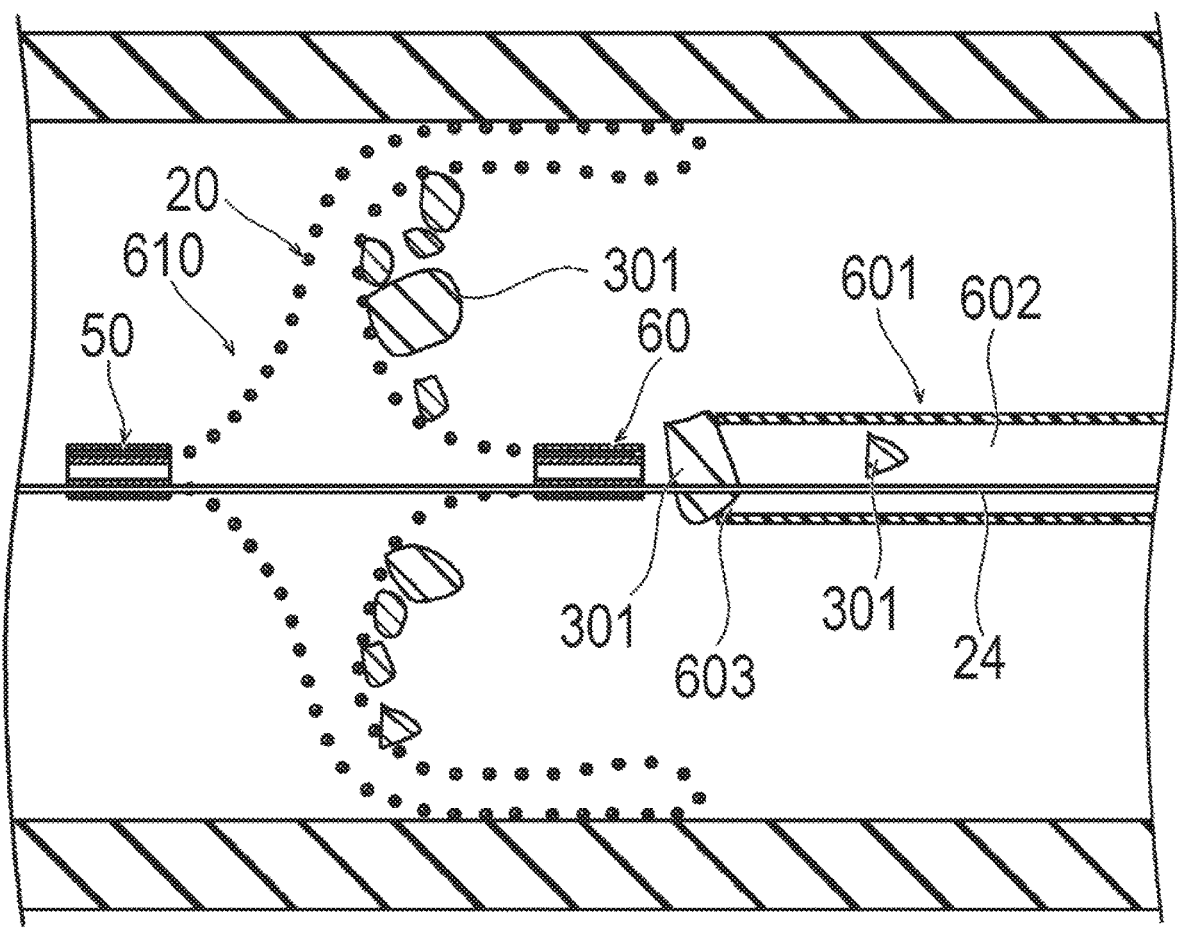
FIG. 30 is a cross-sectional view illustrating a state in which blood clots are suctioned by the suction catheter.

Next, the plunger of the syringe 180 is pulled. Accordingly, a negative pressure is generated in the suction lumen 602. Accordingly, as illustrated in FIG. 30, the blood clots 301 are suctioned from the distal side opening 603 into the suction lumen 602. At this time, small blood clots 301 can pass through the distal side opening 603 and move in the suction lumen 602 toward the proximal side. However, large blood clots 301 cannot pass through the distal side opening 603, are adsorbed by the distal side opening 603, and close the distal side opening 603.

Figure 31:
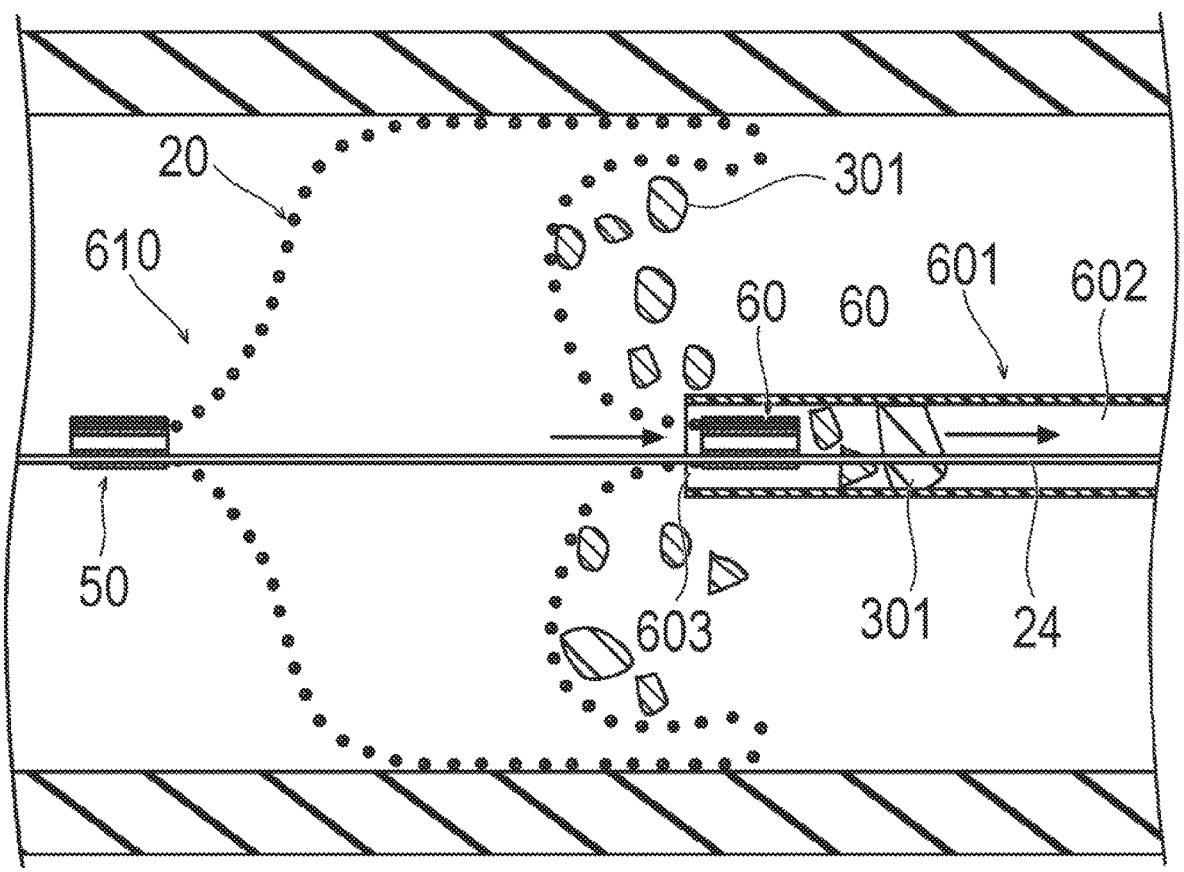
FIG. 31 is a cross-sectional view illustrating a state in which a proximal side coupling portion is inserted into a distal side opening.

Next, as illustrated in FIG. 31, the shaft portion 24 is pulled with the blood clots 301 adsorbed to the distal side opening 603 to move the proximal side coupling portion 60 to the proximal side. Note that the position of the distal side opening 603 of the suction catheter can be fixed within the blood vessel, such that the distal side opening 603 does not shift during the thrombus aspiration operation. Accordingly, the proximal side coupling portion 60 enters the suction lumen 602 from the distal side opening 603. At this time, since the outer diameter of the proximal side coupling portion 60 is larger than the outer diameter of the shaft portion 24, the blood clots 301 adsorbed by the distal side opening 603 are pushed into the suction lumen 602 by the proximal side coupling portion 60. The blood clots 301 pushed into the suction lumen 602 are moved to the proximal side by a negative pressure in the suction lumen 602. Accordingly, a state in which the distal side opening 603 is closed by the blood clots 301 can be eliminated.

Next, in a state in which the position of the distal side opening 603 is fixed, the shaft portion 24 is pushed to move the proximal side coupling portion 60 to the distal side. Accordingly, the proximal side coupling portion 60 is pulled from the distal side opening 603. Accordingly, the distal side opening 603 suctions new blood clots 301 and is closed by large blood clots 301.

Then, the reciprocal movement of the proximal side coupling portion 60 is repeated while making a negative pressure act on the suction catheter 600 by the syringe 180. Accordingly, an action of pushing the blood clots 301 into the suction lumen 602 by the proximal side coupling portion 60 may be repeated. Therefore, even when the blood clots 301 having a size that cannot be collected into the suction lumen 602 only by the suction force are present, the blood clots 301 may be effectively removed by deforming or destructing.

After the suction of the blood clots 301 is completed, the expanding tool 610 is accommodated in the suction catheter 600 and is removed out from the blood vessel to complete the procedure. Note that this method of using only needs to include moving the proximal side coupling portion 60 and the distal side opening 603 relative to each other. Therefore, the distal side opening 603 may be moved in the axial direction with the proximal side coupling portion 60 fixed. Alternatively, both of the proximal side coupling portion 60 and the distal side opening 603 may be moved. Alternatively, the amplitude of the reciprocal movement of the proximal side coupling portion 60 in the axial direction may vary. Alternatively, the method of using described in the third exemplary embodiment may be applied to the suction system according to the first and second exemplary embodiment.

Note that the present disclosure is not limited only to the exemplary embodiments described above, and various modifications may be made by skills in the art within a technical scope of the present disclosure. For example, in the first, second, and third exemplary embodiments, the suction system is configured to access from the upstream side of the target lesion. However, the structure of causing the suction system to access from the downstream side of the target lesion is also applicable.

The biological lumen that allows insertion of the suction system is not limited to the blood vessel, and may be vessels, ureters, bile ducts, fallopian tubes, hepatic ducts and the like.

In the first, second, and third exemplary embodiments, the device to be inserted into the blood vessel along the shaft portion 24 is the breaking device 100 provided with the breaking member 140. However, the configuration of the device to be inserted is not limited as long as the object can be broken. In the present exemplary embodiment, the suction catheter 30 is used as the sheath for accommodating the expansion portion 20 and the closing member 70 and carrying the same to intended positions. However, the sheath for accommodating the expansion portion 20 and the closing member 70 and carrying the same to the intended positions may be a device different from the suction catheter 30.

In the first, second, and third exemplary embodiments, the proximal side coupling portion 60 located on the proximal side of the expansion portion 20 is slidable with respect to the shaft portion 24, and the distal side coupling portion 50 located on the distal side is coupled to the shaft portion 24 (see FIG. 8). However, the proximal side coupling portion located on the proximal side of the expansion portion 20 is coupled to the shaft portion 24, and the distal side coupling portion located on the distal side of the expansion portion 20 may be slidable with respect to the shaft portion 24. Note that being coupled to the shaft portion 24 is not limited to being secured to the shaft portion 24, and being coupled while allowing relative rotation or movement is also included.

In addition, the expansion portion 20 of the suction system 1 does not have to be folded. Likewise, the sheath tubular member does not have to be provided with the bent portion. Alternatively, a plurality of the suction ports may be provided.

The detailed description above describes a suction catheter and a suction system to be inserted into a biological lumen, and a treatment method using the suction system. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for suctioning an object in a blood vessel, the method comprising:
    inserting an expansion portion connected to a shaft portion on a distal portion of the shaft portion into the blood vessel;
    expanding the expansion portion in the blood vessel;
    inserting a suction catheter along the shaft portion into the blood vessel;
    reciprocating at least the expansion portion or the suction catheter relative to each other along an axial axis of the shaft portion;
    breaking the object by a proximal side coupling portion of the expansion portion and the suction catheter; and
    suctioning the object with the suction catheter.

2. The method according to claim 1, further comprising:
    removing the suction catheter and the expansion portion from the blood vessel.

3. The method according to claim 1, wherein after the expanding of the expansion portion, the method further comprising:
    folding a proximal portion of the expansion portion along the axial axis of the shaft portion into a distal side of the proximal portion of the expansion portion.

4. The method according to claim 3, wherein after the folding of the proximal portion of the expansion portion, while fixing a positon of a distal side of the expansion portion, the method further comprising:
    reciprocating only the proximal portion of the expansion portion along the axial axis of the shaft portion.

5. The method according to claim 1, wherein the expanding of the expansion portion in the blood vessel comprises:
    indwelling the expansion member into the blood vessel.

6. The method according to claim 1, wherein the expansion portion comprises:
    a cylindrical member having a plurality of gaps and being resiliently deformable.

7. A method for suctioning an object in a blood vessel, the method comprising:
    inserting an expansion portion connected a shaft portion on a distal portion of the shaft portion into the blood vessel;
    expanding the expansion portion in the blood vessel;
    inserting a suction catheter along the shaft portion into the blood vessel;
    moving a proximal side coupling portion of the expansion portion or the suction catheter along an axial axis of the shaft portion relative to each other along an axial axis of the shaft portion;
    breaking the object by the proximal side coupling portion and the suction catheter; and
    suctioning the object by the suction catheter.

8. The method according to claim 7, further comprising:
    removing the suction catheter and the expansion portion from the blood vessel.

9. The method according to claim 7, wherein after the expanding of the expansion portion, the method comprising:
    folding a proximal portion of the expansion portion along the axial axis of the shaft portion into a distal side of the proximal portion of the expansion portion.

10. The method according to claim 9, wherein after the folding of the proximal portion of the expansion portion, while fixing a positon of a distal side of the expansion portion, the method comprising:
    reciprocating only the proximal portion of the expansion portion along the axial axis of the shaft portion.

11. A method for suctioning an object in a blood vessel, the method comprising:
    inserting an expansion portion connected to a shaft portion on a distal portion of the shaft portion into the blood vessel;
    expanding the expansion portion in the blood vessel;
    inserting a suction catheter along the shaft portion into the blood vessel;
    inserting a breaking device into the blood vessel along the shaft portion;
    breaking the object by the breaking device;
    moving a proximal side coupling portion of the expansion portion or the suction catheter along an axial axis of the shaft portion relative to each other along an axial axis of the shaft portion;
    suctioning a broken object by the suction catheter; and
    removing the suction catheter and the expansion portion from the blood vessel.

12. The method according to claim 11, wherein after the expanding of the expansion portion, the method comprising:
    folding a proximal portion of the expansion portion along the axial axis of the shaft portion into a distal side of the proximal portion of the expansion portion.

13. The method according to claim 11, wherein after the folding of the proximal portion of the expansion portion, while fixing a positon of a distal side of the expansion portion, the method comprising:
    moving only the proximal portion along the axial axis of the shaft portion.

14. The method according to claim 11, wherein the moving of the proximal side coupling portion of the expansion portion or the suction catheter along the axial axis of the shaft portion relative to each other along an axial axis of the shaft portion comprises:

reciprocating the proximal side coupling portion of the expansion portion or the suction catheter along the axial axis of the shaft portion.

15. The method according to claim 11, wherein after the breaking of the object, the method comprising:
removing the breaking device from the blood vessel.

16. The method according to claim 15, wherein after the removing of the breaking device, the method comprising:
moving the suction catheter to the expansion portion and suctioning the broken objects in the folded proximal portion by the suction catheter.

17. The method according to claim 11, wherein the moving the proximal side coupling portion of the expansion portion or the suction catheter along the axial axis of the shaft portion relative to each other along an axial axis of the shaft further comprises:
moving the proximal side coupling portion of the expansion portion to or into a distal opening of the suction catheter to further break the broken object.

18. The method according to claim 11, wherein the expansion portion is a filter.

19. The method according to claim 11, comprising:
generating a negative pressure in the suction catheter by pulling a plunger of a syringe connected to the suction catheter; and
adhering the broken objects to the expansion portion.

\* \* \* \* \*